(12) United States Patent
Calis et al.

(10) Patent No.: US 10,595,517 B2
(45) Date of Patent: Mar. 24, 2020

(54) INSECT SPAWNING CONTAINER, FACILITY AND METHOD FOR BREEDING INSECTS

(71) Applicant: PROTI-FARM R & D B.V., Ermelo (NL)

(72) Inventors: Hans Calis, Ermelo (NL); Pieter Johannes Antonius Franken, Ermelo (NL)

(73) Assignee: Proti-Farm R & D B.V., AB Ermelo (NL)

( * ) Notice: Subject to any disclaimer, the term of this patent is extended or adjusted under 35 U.S.C. 154(b) by 313 days.

(21) Appl. No.: 15/558,345

(22) PCT Filed: Mar. 10, 2016

(86) PCT No.: PCT/NL2016/050168
§ 371 (c)(1),
(2) Date: Sep. 14, 2017

(87) PCT Pub. No.: WO2016/153340
PCT Pub. Date: Sep. 29, 2016

(65) Prior Publication Data
US 2018/0242563 A1  Aug. 30, 2018

(30) Foreign Application Priority Data

Mar. 24, 2015 (NL) .................................... 2014514

(51) Int. Cl.
*A01K 67/00* (2006.01)
*A01K 67/033* (2006.01)
(52) U.S. Cl.
CPC ...... *A01K 67/033* (2013.01); *A01K 2227/706* (2013.01)

(58) Field of Classification Search
CPC ....... A01K 67/00; A01K 67/02; A01K 67/033
(Continued)

(56) References Cited

U.S. PATENT DOCUMENTS 6,561,125 B1 * 5/2003 Lohsomboon ....... A01K 67/033
  119/416
7,998,728 B2 * 8/2011 Rhoads ............... C05F 17/0009
  119/6.7

(Continued)

FOREIGN PATENT DOCUMENTS

CN   2696321 Y    5/2005
JP   S-49-17115 B1   4/1974
(Continued)

OTHER PUBLICATIONS

International Search Report and Written Opinion of PCT/NL2016/050168, dated Nov. 21, 2016, 20 pages.

*Primary Examiner* — Richard T Price, Jr.
(74) *Attorney, Agent, or Firm* — Blank Rome LLP

(57) ABSTRACT

The present invention relates to an insect spawning container in which at least one spawn structure is provided in which the mother insects will spawn their eggs. The spawn structure has a scalable face such that the mother beetles can crawl from the bottom onto and up along the scalable face of the spawn structure, the spawn structure comprising a multitude of crevices accessible from the scalable face, the crevices having dimensions tuned to the egg-laying tube of the mother beetles.

19 Claims, 14 Drawing Sheets

(58) Field of Classification Search
USPC .................................... 119/6.6, 6.7, 6.8, 6.9
See application file for complete search history.

(56) References Cited

U.S. PATENT DOCUMENTS 8,201,518 B2 * 6/2012 Smith .................... A61D 1/025
119/6.6
8,703,477 B2 * 4/2014 Berkson .............. C05F 17/0009
119/6.7
8,985,056 B2 * 3/2015 Chen .................... A01K 67/033
119/417

FOREIGN PATENT DOCUMENTS

NL 2011300 C 2/2015
WO WO-2014/171829 A1 10/2014

* cited by examiner

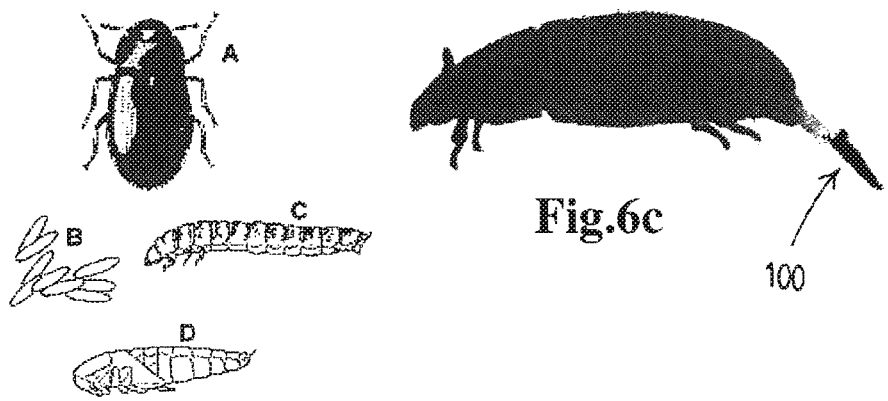
Fig.6a
Fig.6c
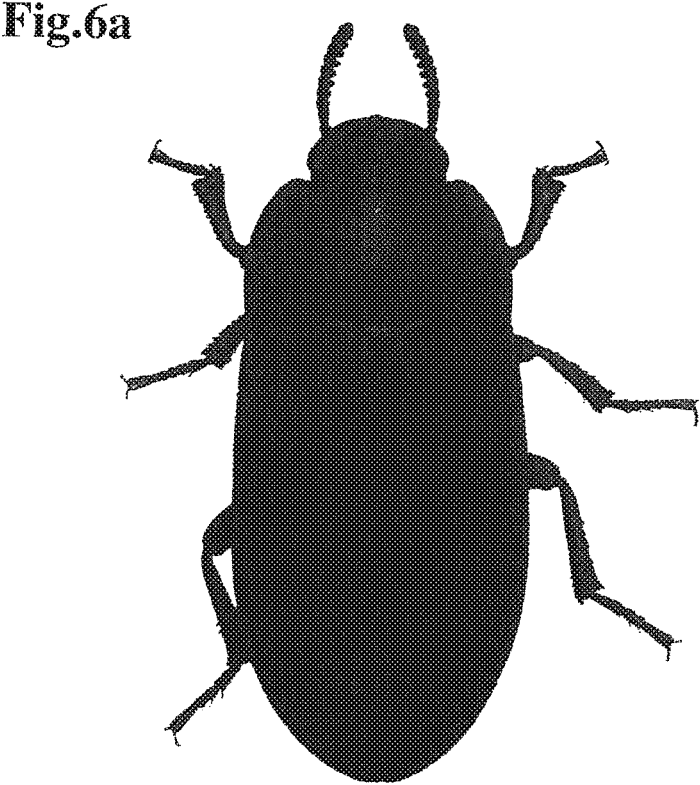
Fig.6b

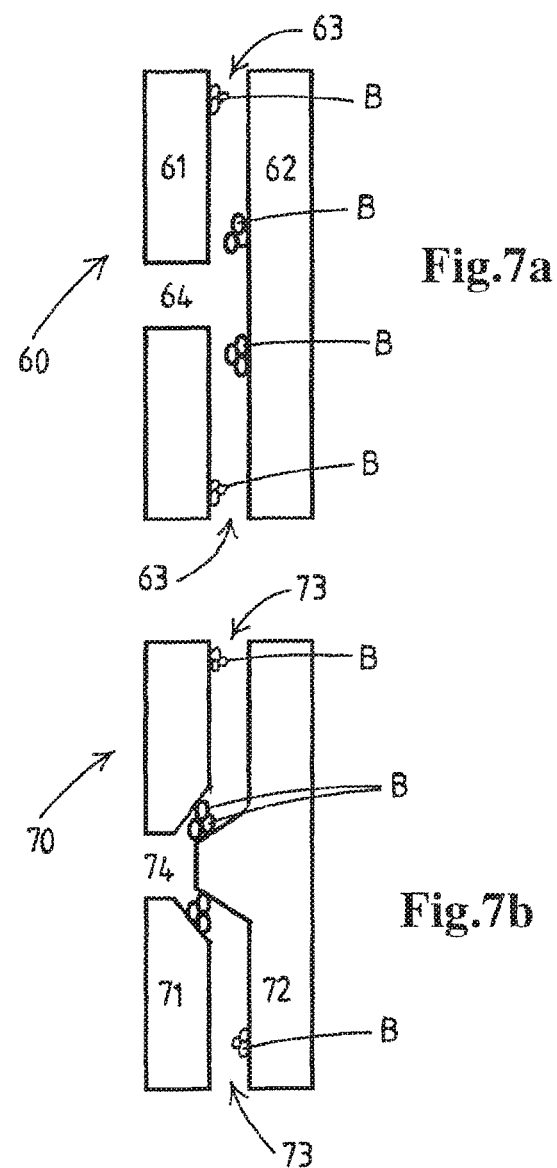

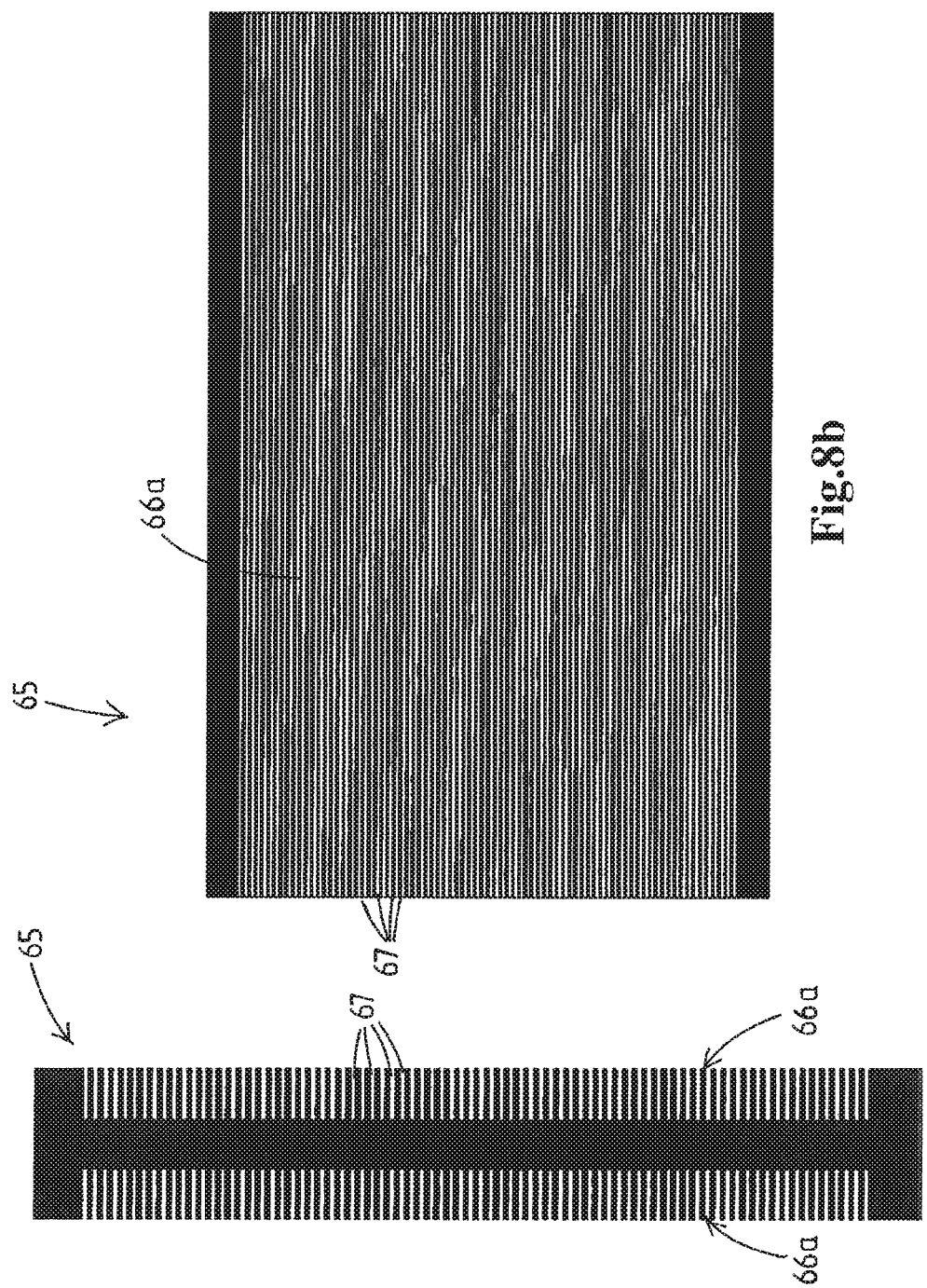

INSECT SPAWNING CONTAINER, FACILITY AND METHOD FOR BREEDING INSECTS

RELATED APPLICATIONS

The present invention is a national phase of PCT/NL2016/050168, filed on Mar. 10, 2016, which claims the benefit of Netherlands Application No. 2014514, filed on Mar. 24, 2015. The entire contents of those applications are hereby incorporated by reference.

BACKGROUND OF THE INVENTION

Field of the Invention

The present invention relates to a method and facility for breeding insects in general, and a particular method and spawn structure for breeding insects of the type with crawling mother beetles having a protractable egg-laying tube.

Description of Related Art

The term breeding refers to the natural process of reproduction, involving spawning—the process of releasing and depositing eggs, and hatching—bringing forth larvae from the egg. It differs from the process of rearing insects, which refers to the process of tending insects from baby-larvae to mature larvae, and possibly also including pupating and emerging into beetles.

Commonly known methods for breeding insects involve the provision of spawning containers adapted to receive adult insects and insect food. In each spawning container one or more removable spawn structures are provided, in which the mother insects will spawn their eggs. Most species will just drop the eggs to the ground, in which event the spawn structure may be a tissue or the like, but other species will stick it in the ground or glue it to the spawning container or other parts, e.g. leaves or other structures provided for. The spawn structure or parts thereof holding the eggs is removable. The eggs are thus harvested and allowed to hatch in a hatch area.

From NL2011300 an insect cage is known, comprising a space, limited by walls, at least one of which is at least partly light translucent. The cage provides a facility to influence the breeding, mating and laying of eggs, by regulating at least a property of the light that is added through the light transparent wall. The cage may be provided with an egg depository device, e.g. comprising a gas permeable material such as a sponge, a plate with holes or small crevices or a specially designed structure. The egg depository device is positioned vertically in a slot in the front wall, at a distance from the bottom.

From WO2014171829 a method and system for rearing insects is known, referring to the process of tending insects from baby-larvae to mature larvae. In a climate area, stacked crates with immature phases of insects are arranged in rows. Periodically, individual crates are conveyed to a feed area provided with an observation station. Based on the observation of a retrieved individual crate it is determined whether supplementary feed stock is to be added, or that the insects are withdrawn from further rearing for harvesting, or discarding from further rearing.

SUMMARY OF THE INVENTION

The use of insects for human consumption being an emerging trend in the Western world, there is a desire for up-scaling insect breeding facilities.

An object of a first and second aspect of the present invention is to provide an improved method and facility for breeding insects, providing a reliable output of baby larvae, suitable for further rearing.

According to a first aspect of the present invention, an insect breeding facility is provided, comprising:
- a spawning area in which a plurality of spawning containers are present which are adapted to receive or have received adult insects including mother insects and insect food, wherein the plurality of spawning containers is stacked in one or more stacks of spawning containers;
- a plurality of spawn structures, wherein at least one spawn structure is adapted to be provided or is provided in each spawning container in the spawning area, in which spawn structures the mother insects will spawn their eggs such that the spawn structure or part of the spawn structure holds the eggs, wherein said spawn structure or said part thereof is removable from the spawning container, leaving the adult insects in the spawning container;
- a hatch area in which the eggs will hatch, which hatch area is adapted to receive said spawn structure or said part thereof holding the eggs and removed from the spawning containers, allowing harvesting of baby larvae;
- a food delivery system to deliver food to the spawning containers;
- a spawn structures handling area comprising a spawn structure handling system, adapted to remove said spawn structure or said part thereof holding the eggs from the spawning container and transport said spawn structure or said part to the hatch area, and to provide an empty spawn structure or part thereof in each spawning container, which spawn structures handling area is preferably also adapted to clean the spawn structures or parts thereof;
- a container handling system to transport the spawning containers between the spawning area and the spawn structures handling area.

The first aspect of the present invention further relates to a method for breeding insects, comprising the steps of:
- providing a spawning area in which a plurality of spawning containers are present which have received adult insects including mother insects and which are adapted to receive or have received insect food, wherein the plurality of spawning containers is stacked in one or more stacks of spawning containers;
- providing at least one spawn structure in each spawning container in the spawning area, in which spawn structures the mother insects will spawn their eggs such that the spawn structure or part of the spawn structure holds the eggs, wherein said spawn structure or said part thereof is removable from the spawning container, leaving the adult insects in the spawning container;
- providing a hatch area in which the eggs will hatch, which hatch area is adapted to receive said spawn structure or said part thereof holding the eggs and removed from the spawning containers, allowing harvesting of baby larvae;
- providing a food delivery system to deliver food to the spawning containers;
- providing a spawn structures handling area comprising a spawn structure handling system, adapted to remove said spawn structure or said part thereof holding the eggs from the spawning container and transport said spawn structure or said part to the hatch area, and to provide an empty spawn structure or part thereof in each spawning container, which spawn structures handling area is preferably also adapted to clean the spawn structures or parts thereof;

providing a container handling system to transport the spawning containers between the spawning area and the spawn structures handling area.

the mother insects spawning their eggs in spawn structures;

periodically:

delivering food to the spawning containers;

transporting the spawning containers from the spawning area to the spawn structures handling area;

removing the spawn structures or parts thereof holding the eggs from the spawning containers by the spawn structure handling system, leaving the adult insects in the spawning container;

transporting said spawn structures or said parts thereof to the hatch area by the spawn structure handling system;

providing an empty spawn structures or parts thereof in each spawning container by the spawn structures handling system;

transporting the spawning containers from the spawn structures handling area to the spawning area by the container handling system;

hatching the eggs in the hatch area, and periodically harvesting baby larvae.

Hence, according to the first aspect of the invention, the spawning containers are stacked, at least during part of the spawning process. Periodically, preferably daily, the spawning containers are transported to a spawn structures handling area wherein the spawn structure or parts thereof holding the eggs is removed from the spawning container. Feeding may take place prior to or after removing the eggs. According to the invention, the eggs are removed by removing the spawn structure or part thereof that holds the eggs from the spawning container and transporting said spawn structures or parts thereof to the hatch area. Such a container handling system for transporting the spawning containers between the spawning area and the spawn structures handling area attributes to efficient up-scaling of the process.

In embodiments, the spawning containers are stacked directly onto each other, and the container handling system is adapted to de-stack the one or more stacks and stack the spawning containers into one or more stacks in the spawning area, and transport individual spawning containers between the spawning area and the spawn structures handling area. Advantageously, the process of stacking, as well as the process of de-stacking, takes place in less than 30 seconds, preferably less than 25 seconds. The container handling system may be adapted to operate in a continuous mode, 24 hours/day.

In embodiments, the insect breeding facility further comprises a feed area comprising the food delivery system, wherein the container handling system is adapted to transport the spawning containers between the spawning area and the feed area.

In embodiments, the container handling system transports individual spawning containers from the spawning area to the feed area and to the spawn structures handling area and then back to the spawning area.

In embodiments, the conditions of the spawning area and hatch area are individually controllable. In particular the requirements related to temperature, humidity and ventilation may differ between these areas. Possibly, also the conditions of the spawn structures handling area, and/or the feed area are individually controllable as well.

In embodiments, the spawning container is of an essentially rectangular shape comprising four corners between which a peripheral wall is provided, wherein the corner portions have a configuration that allows stacking of the trays and provide sufficient strength for heavy loads of stacked trays. Suitable dimensions of a spawning container are e.g. 600*800 mm, or 600*400 mm, having a height of 125 mm. Advantageously, a stack may comprise 30-40 containers, creating a height of up to 5 meters. The weight of such a stack may be up to 200 kg.

As some insects prefer to spawn in cracks the inner surface of the spawning container essentially smooth, free of seams and sharp corners.

In embodiments, the plurality of spawning containers is stacked in multiple stacks of spawning containers. In embodiments, the stacks are oriented in rows of up to 100 stacks, which rows are separated by a ventilation space of 50-100 cm.

In embodiments, in the spawning area spawning container holders are provided, adapted to comprise a stack of spawning containers. This may e.g. be a pallet, but it is also well conceivable that a warehouse construction is provided in the spawning area, in which multiple stacks are stored adjacent and above each other. Alternatively, the spawning container is embodied as a tray, and the spawning container holder as a tray cabinet.

In embodiments, storage racks are provided in which stacks of spawning containers may be stored above each other. In such embodiments, a stack may comprise 15 containers and create a height of 2 meters, above which stack another stack of –2 metres may be stored in the storage rack.

In embodiments, the corner portions of the spawning container define an upper corner support surface and a bottom corner support surface. Advantageously, the upper and bottom corner support surface have interlocking configurations allowing the trays to be stacked. For example, the corner support surfaces may be provided with protrusions and corresponding indentations, allowing the spawning containers to be stably stacked reducing the risk of sliding sideways.

In alternative embodiments, in the spawning area stacking elements are provided, which are positionable between two spawning containers to form a stack of spawning containers. In embodiments, the upper and bottom corner support surfaces are adapted to allow the stacking elements to be positioned between the upper corner support surface of a first spawning container and the bottom corner support surface of a second spawning container.

In embodiments, a bottom of the spawning container is provided with a perforated area to allow the removal of excrements, and wherein in the spawning area below a stack of such spawning containers an excrement collection tray is positioned. Advantageously, this perforated area is provided remote from the area in the spawning container in which the food is delivered. In embodiments, the perforated area is also remote from the spawn structures in the spawning container. In embodiments, the perforated area is provided centrally in the spawning container. In embodiments, one, two or even more perforated areas are provided. Advantageously, the perforated area covers 10-30% of the total bottom surface of the spawning container.

The perforated area has preferably openings of a dimension allowing the removal of excrements (droppings), but preventing adult insects from being trapped in the opening. For lesser mealworms, a preferred maximum dimension of the openings is 2-6 mm.

It is conceivable that the perforated area is formed integral with the spawning container, e.g. in an injection molding process. Alternatively, the bottom of the spawning container is provided with an opening in which a mesh is provided. Such a mesh may e.g. be made of nylon or stainless steel. As some insects prefer to spawn in cracks, a mesh is advantageously provided while maintaining the inner surface of the spawning container essentially smooth, free of seams and sharp corners.

In embodiments, the spawning container comprises a peripheral wall provided with ventilation openings to allow for the dissipation of heat and $CO_2$. To obtain optimum spawning conditions, the circumstances in the spawning area of the insect breeding center, such as temperature, humidity and ventilation, are advantageously controllable. To control the circumstances in each spawning container, it is thus preferred to provide one or more ventilation openings. Advantageously, the ventilation openings cover 10-50%, more preferably between 30-40% of the peripheral wall. Advantageously, ventilation openings are provided on opposite sides of the peripheral wall.

In embodiments wherein the spawning container is of an essentially rectangular shape comprising four corners between which four sides are provided, possibly at least a portion of the one or more sides is dropped to provide a ventilation opening.

In embodiments, a preparation and cleaning area is provided to periodically remove the adult insects from the spawning containers, clean the spawning containers and place new adult insects including mother insects into the spawning containers.

Advantageously, in the spawn structures handling area periodically cleaning of the spawn structures is made possible.

According to a second aspect of the invention, a method for breeding insects is provided, comprising the steps of:
  providing a spawning area in which a plurality of batches of spawning containers is present which have received adult insects including mother insects and which are adapted to receive or have received insect food;
  providing at least one spawn structure in each spawning container in the spawning area, in which spawn structures the mother insects will spawn their eggs such that the spawn structure or part of the spawn structure holds the eggs, wherein said spawn structure or said part thereof is removable from the spawning container, leaving the adult insects in the spawning container;
  providing a hatch area, which hatch area comprises a plurality of hatching chambers corresponding in number with the number of batches of spawning containers, in which hatching chambers the eggs will hatch, which hatch area is adapted to receive said spawn structure or said part thereof holding the eggs and removed from the spawning containers, allowing harvesting of baby larvae, wherein an $n^{th}$ hatching chamber is adapted to receive the spawn structures or parts of the spawn structures that hold the eggs of a corresponding $n^{th}$ batch of spawning containers;
  the mother insects spawning their eggs in spawn structures;
  providing a food delivery system and periodically delivering food to the spawning containers;
  providing a spawn structures handling area comprising a spawn structure handling system, adapted to remove said spawn structure or said part thereof holding the eggs from the spawning container and transport said spawn structure or said part to the hatch area, and to provide an empty spawn structure or part thereof in each spawning container, which spawn structures handling area is preferably also adapted to clean the spawn structures or parts thereof;
  providing a container handling system to transport the spawning containers between the spawning area and the spawn structures handling area;
  the mother insects spawning their eggs in spawn structures;
  periodically:
    transporting the spawning containers from the spawning area to the spawn structures handling area;
    removing the spawn structures or parts thereof holding the eggs from the batches of spawning containers by the spawn structure handling system, leaving the adult insects in the spawning container;
    transporting said spawn structures or said parts thereof to the corresponding hatching chamber in the hatch area by the spawn structure handling system;
    providing an empty spawn structures or parts thereof in each spawning container by the spawn structures handling system;
    transporting the spawning containers from the spawn structures handling area to the spawning area by the container handling system;
hatching the eggs in the hatching chambers, and periodically harvesting baby larvae.

The second aspect of the invention also relates to an insect breeding facility comprising:
  a spawning area in which a plurality of batches of spawning containers are present which are adapted to receive or have received adult insects including mother insects and insect food, wherein the plurality of spawning containers is stacked in one or more stacks of spawning containers;
  a plurality of spawn structures, wherein at least one spawn structure is adapted to be provided or is provided in each spawning container in the spawning area, in which spawn structures the mother insects will spawn their eggs such that the spawn structure or part of the spawn structure holds the eggs, wherein said spawn structure or said part thereof is removable from the spawning container, leaving the adult insects in the spawning container;
  a hatch area comprising a plurality of hatching chambers corresponding in number with the number of batches of spawning containers, in which hatching chambers the eggs will hatch, which hatch area is adapted to receive said spawn structure or said part thereof holding the eggs and removed from the spawning containers, allowing harvesting of baby larvae, wherein an $n^{th}$ hatching chamber is adapted to receive the spawn structures or parts of the spawn structure that holds the eggs of a corresponding $n^{th}$ batch of spawning containers,
  a spawn structures handling area comprising a spawn structure handling system, adapted to remove said spawn structure or said part thereof holding the eggs from the spawning container and transport said spawn structure or said part to the hatch area, and to provide an empty spawn structure or part thereof in each spawning container, which spawn structures handling area is preferably also adapted to clean the spawn structures or parts thereof;
  a container handling system to transport the spawning containers between the spawning area and the spawn structures handling area.

The effect of providing corresponding numbers of batches of spawning containers and hatching chambers is that each batch of harvested baby larvae from a hatching chamber can be tracked to the batch of spawning containers with the mother insects of these baby larvae.

As such, the productivity of the mother insects can easily be monitored, as well as the influence of insect food, temperature etc. As a result, it is possible to timely replace a batch of spawning containers in case of reduced productivity. On the other hand, it is also possible to maintain a batch of highly productive spawning containers longer in the spawning area than envisaged. This ensures a flexibility in the amount of baby larvae that is produced. Furthermore, advantageously, in view of historical data of productivity of batches of spawning containers and corresponding harvested baby larvae numbers, the numbers of baby larvae yet to be harvested can be predicted.

It is noted that it is conceivable that during insect breeding, in certain periods of time, the number of batches of spawning containers does not exactly match the number of hatching chambers. Advantageously, a buffer with a number of spare spawning containers is available, and/or a buffer with a number of spare hatching chambers is provided.

In embodiments, the number of batches of spawning containers corresponds to the periodicity with which adult insects are removed from the spawning containers. For example, in embodiments in which the adult beetle is allowed to spawn its eggs during 140 days, after which they are removed, also 140 batches of spawning containers and 140 hatching chambers are provided. As such, a continuous production is assured. It is conceivable that in view of flexibility, a slightly larger number of batches of spawning containers and hatching chambers is provided, e.g. 150. Advantageously, frequently an old batch of spawning containers is cleaned and a new batch of spawning containers with new adult insects is provided. For example, every day a new batch of 50 spawning containers is provided in the spawning area.

According to the second aspect of the invention, the spawn structures handling system transports the spawn structures or said parts thereof to the corresponding hatching chamber. In embodiments, the hatching chambers are provided mobile. Consequently, a corresponding hatching chamber can be positioned in the vicinity of the spawn structures handling area to receive the corresponding spawn structures.

Advantageously, the baby larvae are collected in a baby larvae collection container. Preferably, each hatching chamber is provided with a corresponding baby larvae collection container, allowing the baby larvae in a particular collection container to be tracked to the batch of spawning containers with the mother insects of these baby larvae.

In embodiments, a preparation and cleaning area is provided to periodically remove the adult insects from the spawning containers, clean the spawning containers and place new adult insects including mother insects into the spawning containers.

Advantageously, in the spawn structures handling area periodically cleaning of the spawn structures is made possible.

An object of a third aspect of the present invention is to provide an improved method and facility for breeding insects of the type with crawling mother beetles having a protractable egg-laying tube, such as lesser mealworms or *Zophobas morios*, which is suitable for up-scaling.

The lesser mealworm is formally known as *Alphitobius diaperinus*, and is a species of beetle in the family Tenebrionidae, the darkling beetles. The larvae, like certain other mealworms, are suitable for consumption. As pet food they have been called buffalo worms. *Zophobas morio* is also a species of darkling beetle, whose larvae are known by the common name superworm or *zophobas*.

The adult female beetle of the lesser mealworm lays usually about 400-900 eggs, but it has been known to produce up to 2000. It lays eggs every few days throughout its life, which is generally up to one year long. It deposits the eggs in litter, droppings, grain stores, or cracks in structures. The larvae emerge within a week and take 40 to 100 days to reach maturity, depending on conditions and the food supply.

The tiny, white, bean-shaped eggs of the lesser mealworm are about 1.5 millimeters long. The larvae measure up to 20 millimeters long at its final sub-adult stage. It is tapering and segmented, with three pairs of legs toward the front end. It is whitish when newly emerged from the egg and it darkens to a yellow-brown. It becomes pale when preparing to molt (shed its exoskeleton) between instar stages. It then enters the pupal stage. The pupa does not eat and seems inactive, but it is transforming itself into a beetle. After pupating, a white adult beetle emerges from the pupa. It soon turns brown and then almost black. The adult lesser mealworm beetle is roughly 6 millimeters long and widely oval in shape.

The third aspect of the present invention relates to an insect spawning container to be used in an insect breeding facility for breeding insects of the type with crawling mother beetles having a protractable egg-laying tube, such as lesser mealworms or *Zophobas morios*, in which insect spawning container at least one spawn structure is provided in which the mother insects will spawn their eggs, wherein the insect spawning container comprises a bottom, and the at least one spawn structure adjoins the bottom, the at least one spawn structure having a scalable face such that the mother beetles can crawl from the bottom onto and up along the scalable face of the spawn structure, the at least one spawn structure comprising a multitude of crevices accessible from the scalable face, the crevices having dimensions tuned to the egg-laying tube of the mother beetles.

The third aspect of the present invention further relates to an insect spawning container to be used in an insect breeding facility for breeding insects of the type with crawling mother beetles having a protractable egg-laying tube, such as lesser mealworms or *Zophobas morios*, the spawning container being provided with at least one spawn structure, in which spawn structure the mother insects will spawn their eggs, the spawn structure comprising a first part and a second part which are movable with respect to each other allowing an increase and decrease of the mutual distance, wherein for the purpose of spawning the first and a second part of the spawn structures are positionable with respect to each other such that a multitude of crevices is created therebetween, and wherein for the purpose of hatching and/or cleaning the distance between the first and second part of the spawn structure is adapted to be increased.

The third aspect of the invention further relates to an insect breeding facility for breeding insects of the type with crawling mother beetles having a protractable egg-laying tube, such as lesser mealworms or *Zophobas morios*, comprising:

a spawning area in which a plurality of spawning containers are present which are adapted to receive or have received adult insects including mother insects and insect food;

a plurality of spawn structures, wherein at least one spawn structure is adapted to be provided or is provided in each spawning container in the spawning area, in which spawn structures the mother insects will spawn their eggs such that the spawn structure or part of the spawn structure holds the eggs, wherein said spawn structure or said part thereof is removable from the spawning container, leaving the adult insects in the spawning container;

a hatch area in which the eggs will hatch, which hatch area is adapted to receive said spawn structure or said part thereof holding the eggs and removed from the spawning containers, allowing harvesting of baby larvae;

a food delivery system to deliver food to the spawning containers;

a spawn structures handling area comprising a spawn structure handling system, adapted to remove said spawn structure or said part thereof holding the eggs from the spawning container and transport said spawn structure or said part to the hatch area, and to provide an empty spawn structure or part thereof in each spawning container, which spawn structures handling area is preferably also adapted to clean the spawn structures or parts thereof;

a container handling system to transport the spawning containers between the spawning area and the spawn structures handling area.

The third aspect of the invention further relates to an insect breeding facility for breeding insects of the type with crawling mother beetles having a protractable egg-laying tube, such as lesser mealworms or *Zophobas morios*, comprising:

a spawning area in which a plurality of spawning containers are present which are adapted to receive or have received adult insects including mother insects and insect food;

a plurality of spawn structures, wherein at least one spawn structure is adapted to be provided or is provided in each spawning container in the spawning area, in which spawn structures the mother insects will spawn their eggs such that the spawn structure or part of the spawn structure holds the eggs, wherein said spawn structure or said part thereof is removable from the spawning container, leaving the adult insects in the spawning container; wherein each spawn structure comprises a first part and a second part which are movable with respect to each other allowing an increase and decrease of the mutual distance, wherein for the purpose of spawning the first and a second part of the spawn structure are positionable with respect to each other such that a multitude of crevices is created therebetween;

and wherein for the purpose of hatching and/or cleaning the distance between the first and second part of the spawn structure is adapted to be increased;

a hatch area in which the eggs will hatch, which hatch area is adapted to receive said spawn structure or said part thereof holding the eggs and removed from the spawning containers, allowing harvesting of baby larvae;

a food delivery system to deliver food to the spawning containers;

a spawn structures handling area comprising a spawn structure handling system, adapted to remove said spawn structure or said part thereof holding the eggs from the spawning container and transport said spawn structure or said part to the hatch area, and to provide an empty spawn structure or part thereof in each spawning container, which spawn structures handling area is preferably also adapted to clean the spawn structures or parts thereof;

a container handling system to transport the spawning containers between the spawning area and the spawn structures handling area.

The third aspect of the invention further relates to a method for breeding insects of the type with crawling mother beetles having a protractable egg-laying tube, such as lesser mealworms or *Zophobas morios*, comprising the steps of:

providing a spawning area in which a plurality of spawning containers are present which have received adult insects including mother insects and which are adapted to receive or have received insect food;

providing at least one spawn structure in each spawning container in the spawning area, in which spawn structure the mother insects will spawn their eggs such that the spawn structure or part of the spawn structure holds the eggs, wherein said spawn structure or part thereof is removable from the spawning container, leaving the adult insects in the spawning container, providing a hatch area in which the eggs will hatch, which hatch area is adapted to receive said spawn structure or said part thereof holding the eggs and removed from the spawning containers, allowing harvesting of baby larvae;

providing a food delivery system to deliver food to the spawning containers;

providing a spawn structures handling area comprising a spawn structure handling system, adapted to remove said spawn structure or said part thereof holding the eggs from the spawning container and transport said spawn structure or said part to the hatch area, and to provide an empty spawn structure or part thereof in each spawning container, which spawn structures handling area is preferably also adapted to clean the spawn structures or parts thereof;

providing a container handling system to transport the spawning containers between the spawning area and the spawn structures handling area;

the mother beetles spawning their eggs in the crevices of the spawn structures, periodically:
delivering food to the spawning containers;
transporting the spawning containers from the spawning area to the spawn structures handling area;
removing the spawn structures or parts thereof holding the eggs from the spawning containers by the spawn structure handling system, leaving the adult insects in the spawning container;
transporting said spawn structures or said parts thereof to the hatch area by the spawn structure handling system;
providing an empty spawn structures or parts thereof in each spawning container by the spawn structures handling system;
transporting the spawning containers from the spawn structures handling area to the spawning area by the container handling system;

hatching the eggs in the hatch area, and periodically harvesting baby larvae.

The third aspect of the invention further relates to a method for breeding insects of the type with crawling mother beetles having a protractable egg-laying tube, such as lesser mealworms or *Zophobas morios*, comprising the steps of:

providing a spawning area in which a plurality of spawning containers are present which have received adult insects including mother insects and which are adapted to receive or have received insect food;

providing at least one spawn structure in each spawning container in the spawning area, in which spawn structure the mother insects will spawn their eggs such that the spawn structure or part of the spawn structure holds the eggs, wherein said spawn structure or part thereof is removable from the spawning container, leaving the adult insects in the spawning container; wherein each spawn structure comprises a first part) and a second part which are movable with respect to each other allowing an increase and decrease of the mutual distance, providing a hatch area in which the eggs will hatch, which hatch area is adapted to receive said spawn structure or said part thereof holding the eggs and removed from the spawning containers, allowing harvesting of baby larvae;

providing a food delivery system to deliver food to the spawning containers;

providing a spawn structures handling area comprising a spawn structure handling system, adapted to remove said spawn structure or said part thereof holding the eggs from the spawning container and transport said spawn structure or said part to the hatch area, and to provide an empty spawn structure or part thereof in each spawning container, which spawn structures handling area is preferably also adapted to clean the spawn structures or parts thereof;

providing a container handling system to transport the spawning containers between the spawning area and the spawn structures handling area;

positioning the first and a second part of the spawn structures with respect to each other such that a multitude of crevices is created therebetween, allowing the mother beetles to spawn their eggs in the crevices onto the first and/or second part of the spawn structures, periodically:
  delivering food to the spawning containers;
  transporting the spawning containers from the spawning area to the spawn structures handling area;
  increasing the distance between the first and second part of the spawn structure,
  removing the spawn structures or parts thereof holding the eggs from the spawning containers by the spawn structure handling system, leaving the adult insects in the spawning container;
  transporting said spawn structures or said parts thereof to the hatch area by the spawn structure handling system;
  providing an empty spawn structures or parts thereof in each spawning container by the spawn structures handling system;
  transporting the spawning containers from the spawn structures handling area to the spawning area by the container handling system;
hatching the eggs in the hatch area, and periodically harvesting baby larvae.

This invention is based on one or more of the insights that insects of which the crawling mother beetles have a protractable egg-laying tube, such as lesser mealworms or Zophobas morios, prefer to spawn in crevices, and that the consumption of eggs adversely affects the number of harvested baby larvae, and that the optimum conditions for hatching the eggs differ from those for spawning eggs.

In embodiments for breeding lesser mealworms the width of the crevices is 0.2-1.2 mm, based on the diameter of the ovipositor (egg-laying tube) of the lesser mealworm. The width of the crevices for breeding Zophobas morios is 0.2-1.8 mm. It is noted that in the wider crevices, e.g. above 1.0 mm for the lesser mealworms and above 1.5 mm for the Zophobas morios, the egg-laying efficiency of the mother beetles may be reduced. Above the above-indicated width, the mothers no longer deposit the eggs, but simply releases/scatters the eggs. It is equally conceivable that the efficiency reduces when the width is smaller, in the lower part of the above-indicated ranges.

The depth of the crevices is 0.5-10.0 mm. In case the crevices are too shallow, the beetles may eat the eggs. In general, the deeper the crevices, the more eggs can be deposited therein, with the risk that the crevices become clogged with eggs.

The crevices may have any shape of cross-section: e.g. circular, square, triangular or polygonal. In embodiments, the cross-section of the crevices is uniform. In embodiments, the crevice tapers outwards towards the side of the spawn structure where the mother insects are provided, facilitating the entry of beetle. It is conceivable that the crevices are elongated, hence having a width and depth tuned to the egg-laying tube of the mother beetles, and a length allowing multiple mother beetles to deposit eggs adjacent each other.

In embodiments, the insect spawning container comprises a bottom, and the at least one spawn structure adjoins the bottom, the at least one spawn structure having a scalable face such that the mother beetles can crawl from the bottom onto and up along the scalable face of the spawn structure, wherein the multitude of crevices is accessible from the scalable face. This is advantageous as it troubles the beetles from eating the eggs, and as it prevents the crevices from being blocked by excrements and/or food. Furthermore, relatively large spawning areas are obtained in view of the footprint of the spawning container. In such embodiments, prior to the removal of the spawn structure or part thereof that holds the eggs from the spawning container, the mother beetles still present on the spawn structure are shaken off and/or wiped from and/or blown off said spawn structure or part thereof. In embodiments, the scalable face has an essentially vertical orientation.

The spawn structure may be made from metal, ceramics or plastics. The latter is preferred in view of costs. The dimensions of a spawn structure may e.g. be 100×300×5 mm.

In embodiments, the bottom of the spawning container is provided with a perforated area to allow the removal of excrements. This has been further explained in relation to the first aspect of the invention, and is also applicable for the third aspect of the invention.

In embodiments, an enlarged area (free space) around the eggs is desired to optimize the hatching climate. The eggs are quite vulnerable and when hatching out, the baby larvae need more space to get out of the crevices. When the crevices are too small, risks are that moisture the eggs become moist, and that the larvae stick to the walls of the crevice. It is conceivable that the enlarged area is created at the start of the hatching process, or only at the end after several days of hatching, or therebetween. The enlarged area may also only be obtained for the purpose of harvesting the baby larvae. It is also conceivable that the enlarged area is obtained only for the purpose of cleaning the spawn structure.

The third aspect of the present invention further relates to an insect spawning container to be used in an insect breeding facility for breeding insects of the type with crawling mother beetles having a protractable egg-laying tube, such as lesser mealworms or *Zophobas morios*, the spawning container being provided with at least one spawn structure, in which spawn structure the mother insects will spawn their eggs, the spawn structure comprising a first part and a second part which are movable with respect to each other allowing an increase and decrease of the mutual distance, wherein for the purpose of spawning the first and a second part of the spawn structures are positionable with respect to each other such that a multitude of crevices is created therebetween, and wherein for the purpose of hatching and/or cleaning the distance between the first and second part of the spawn structure is adapted to be increased.

Such a spawn structure comprising a first and a second part which are movable with respect to each other allows an increase and decrease of the mutual distance. For the purpose of spawning the first and a second part of the spawn structures are positioned with respect to each other such that a multitude of crevices is created therebetween. Advantageously, the spawn structure has a dimension allowing the entry and passage of a protracted egg-laying tube of the beetle into the crevice, to deposit her eggs in the crevices onto the first and/or second part of the spawn structures during spawning, while prohibiting the entry of the mouth into the crevice, and thus preventing the beetles to eat the eggs.

For example the purpose of hatching the distance between the first and second part of the spawn structure is increased to enlarge the area around the eggs. Increasing the distance can also be advantageous for the purpose of cleaning.

In an optional method, the entire spawn structure is removed from the spawning container, and in a subsequent step the distance between the parts of the spawn structure is increased, allowing the first and/or second part of the spawn structure comprising the eggs to be transported to the hatch area.

The deposition of eggs involves sticking the eggs onto a part of the spawn structure. In particular, embodiments are conceivable wherein the first part of the spawn structure is non-sticking, and the eggs are spawned onto the second part of the spawn structure. Advantageously, in such embodiments, the second part of the spawn structure comprising the eggs is removed from the spawning container and transported to the hatch area with a relatively high frequency, e.g. daily. The first part of the spawn structure may also periodically be replaced, but with a lower frequency, e.g. weekly.

In embodiments wherein the first part of the spawn structure is non-sticking, and the eggs are spawned onto the second part of the spawn structure, and wherein the first and second part of the spawn structure are provided movable with respect to each other in the spawning container, an optional method allows the distance between the first and second part of the spawn structure to be increased in the spawning container prior to removing the second part of the spawn structure comprising the eggs from the spawning container and transporting it to the hatch area. Hence, the first part of the first spawn structure is allowed to maintain in the spawning container, while exchanging the second part of the first spawn structure comprising the eggs with a second part, not comprising eggs.

In embodiments wherein the first part of the spawn structure is non-sticking, this part may be produced from a different type of material, or provided with a non-stick coating. Such materials or coatings known from cookware are e.g. polytetrafluoroethylene (PTFE), which is sold under the brand name "Teflon", anodized aluminum, ceramics, silicone, enameled cast iron, and seasoned cast iron. It is also conceivable that the first part of the spawn structure is provided with a disposable non-stick surface, such as parchment paper or bakery release paper.

In embodiments, the spawn structure comprises a first, second and third part which are movable with respect to each other allowing an increase and decrease of the mutual distance, wherein for the purpose of spawning the first and a second part of the spawn structures are positionable with respect to each other such that a multitude of crevices is created therebetween, and the second and third part of the spawn structures are also positionable with respect to each other such that a multitude of crevices is created therebetween, and wherein for the purpose of hatching the distance between the first, second and third part of the spawn structure is adapted to be increased to enlarge the area around the eggs.

In such embodiments, the number of crevices in which beetles will spawn is doubled within a single spawn structure. In advantageous embodiments, both the first and the third part of the spawn structure is non-sticking, and all eggs are spawned on both sides of the second part of the spawn structure. This is advantageous in that only this second part of the spawn structure holds the eggs, and is thus to be placed in the hatch area.

In embodiments, the parts of the spawn structure are embodied as plates. This is in particularly beneficial for mass production. In embodiments, distance keepers are provided between plates to position the first and a second part of the spawn structures with respect to each other to create a multitude of crevices there between.

In embodiments, crevices are created between the first and second parts of the spawn structure by providing slits or borings in the first plate. These borings may a circular or other-shaped cross-section. Preferably, the cross-section of the boring, or width of the slit is 7 mm+1-1 mm for lesser mealworms, and 10 mm+1-1 mm for *Zophobas morios*. The mutual distance between borings is e.g. over 8 mm, preferably over 10 mm, preferably between 10-15 mm.

According to all aspects of the invention a spawning area is provided, comprising a plurality of spawning containers which are adapted to receive adult insects and insect food.

The spawning containers according to all aspects of the invention can be made of any type of material: plastic, metal, glass, ceramics, etc., although plastic is preferred in view of the weight. In embodiments, the spawning container is made from a plastic, preferably a thermoplastic polymer such as polyethylene (PE) or polypropylene (PP). Advantageously, the spawning containers are resistant to cleaning temperatures (which may be over 55° C.), and resistant to attack from cleaning solutions and disinfectants. Furthermore, advantageously the spawning containers are adapted to withstand elevated operation temperatures, up to 40° C. or even up to 50° C. Furthermore, advantageously the spawning containers have a load capacity of at least 10-20 kg, preferably 12-17 kg. For track and trace purposes, the spawning container is advantageously provided with a recognition device, such as a barcode or RFID chip.

Depending on the type of insect, in particular whether the insect is able to fly or not, the spawning containers may have an open top or not. In embodiments, the inner surface of the spawning container is essentially smooth. This may prevent the beetles from escaping the container. In embodiments, no seams or sharp corners are present in the spawning container, in which material placed in the tray may be trapped. Furthermore, as it is desired that spawning takes place in the spawn structures, seams or other irregularities should be avoided to prevent the insect from deposit their eggs therein. Advantageously, smooth and rounded transitions are provided between the bottom and the one or more peripheral walls.

In embodiments, the spawning containers are stacked. For example, the spawning containers are embodied as trays in a tray cabinet. In any event, sufficient ventilation is provided for the adult insects in the spawning container to allow for the dissipation of heat and $CO_2$. For example, perforated areas are provided in the spawning container, e.g. at the top and/or at the sides. To obtain optimum spawning conditions, the circumstances in the insect breeding center, such as temperature, humidity and ventilation, are advantageously controllable. To control the circumstances in each spawning container, it is thus preferred to provide one or more ventilation openings. In embodiments wherein the top of the spawning containers is provided with a cover, or covered by another stacked spawning container, the peripheral walls of the container are preferably provided with ventilation openings. Advantageously, the ventilation openings cover 10-50%, more preferably between 30-40% of the peripheral wall. Advantageously, ventilation openings are provided on opposite sides of the peripheral wall. In embodiments wherein the spawning container is of an essentially rectangular shape comprising four corners between which four sides are provided, advantageously at least a portion of the one or more sides is dropped to provide a ventilation opening.

It is noted that in embodiments according to all aspects of the invention, a bottom of the spawning container is provided with a perforated area to allow the removal of excrements. This has been explained above in relation to the first aspect of the present invention, but is thus applicable to all aspects of the present invention.

The spawning containers are adapted to receive insect food and possibly also water. Examples of insect food are flour, chicken meal, brewery spent grain, egg-powder, fruit such as apples, etc. etc. The spawning containers are possibly provided with dedicated feeding zones, remote from the spawn structures, and, if provided, also remote from the perforated bottom areas.

According to all aspects of the invention, at least one spawn structure is provided in each spawning container, in which spawn structure the mother insects will spawn their eggs such that the spawn structure or part of the spawn structure holds the eggs, wherein said spawn structure or part thereof is removable from the spawning container, leaving the adult insects in the spawning container. The type of spawn structure according to the first and second aspects of the invention is highly dependent of the type of insect that is being bred. Some insects prefer to deposit eggs in cracks, others on leaves or branches or in chambers hollowed out in soil (such as crickets). Such spawn structures may e.g. be provided in a box or tray, or formed as an assembly of multiple parts forming the desired cracks.

In embodiments, the spawning container is provided with one or more spawn structure holders, mounted to or formed integral with the spawning container, for holding at least one spawn structure, wherein the entire spawn structure or at least the part thereof that holds the eggs is removable from the spawn structure holder, leaving the adult insects in the spawning container. In embodiments, the spawn structure holder is adapted to hold multiple spawn structures at a mutual distance.

The hatch area in which the eggs will hatch is according to all aspects of the present invention adapted to receive the spawn structures or parts of the spawn structure that hold the eggs. In embodiments, the hatch area receives the spawn structure or parts thereof holding the eggs in a vertical orientation, allowing the baby larvae to fall downwards as a result of gravity. A height of drop of 30-40 cm is generally no problem for the baby larvae. Possibly, during harvesting the baby larvae from the hatch area, the baby larvae are shaken off or wiped off the spawn structure or part of the spawn structure. The baby larvae are periodically harvested, advantageously daily. In embodiments, the hatch area comprises one or more baby larvae collection containers provided below the spawn structures or parts of the spawn structure that holds the eggs.

In the hatch area, eggs will hatch. The hatching time depends on the type of insect, and may vary e.g. between several days to several weeks. For lesser mealworms, the hatching time is 5-8 days. Baby larvae are periodically harvested from the hatch area. In embodiments wherein spawn structures or parts thereof are provided to a hatch area with a higher frequency than the hatching time, the harvesting frequency may be higher as well. E.g., if daily new spawn structures or parts thereof are provided to a hatch area, baby larvae may be harvested from that hatch area daily as well. If, in an alternative setting, only once a week new spawn structures or parts thereof are provided to a hatch area, the baby larvae may be harvested from that hatch area weekly as well.

The hatch area is adapted to receive the spawn structures or part of the spawn structures that hold the eggs. Each hatch area may be embodied to receive up to several hundreds of spawn structures or parts thereof. It is noted that according to the second aspect of the invention, the hatch area comprises a plurality of hatching chambers. In embodiments, the hatch area or a hatching chamber comprises a plurality of hatching containers, each adapted to receive multiple spawn structures or parts thereof, e.g. up to 100 spawn structures or parts thereof that hold the eggs. The dimensions of such a hatching container are e.g. 400*600 mm. Multiple hatching containers may be stacked on top of each other in a hatching chamber. A baby larvae collection container may be provided below each hatching container or each stack of hatching containers.

The hatch area thus periodically receives a number of spawn structures of parts thereof from the spawning containers. Furthermore, baby larvae are periodically harvested from the hatch area. Advantageously, logistics are available in the hatch area to receive spawn structures holding eggs, remove empty spawn structures and remove baby larvae. In embodiments comprising hatching containers, a container handling device is advantageously provided receiving new hatching containers that have received the spawn structures or parts of the spawn structure that hold the eggs and removing hatching containers with empty spawn structures or parts thereof, and possibly also the baby larvae collection container(s).

According to all aspects of the invention an spawn structures handling area is provided, adapted to remove the spawn structure or parts thereof holding the eggs from the spawning container and transport said spawn structure or said part to the hatch area, and to provide an empty or clean spawn structure or part thereof in each spawning container. Possibly, such spawn structures handling area is also adapted to clean the spawn structures. According to all aspects of the invention, the eggs are removed periodically from the spawning container. For example, the eggs are removed daily, or twice a day, or every other day. Other frequencies are also conceivable. The cleaning frequency of the spawn structures may correspond to the removal frequency, but it is also conceivable that the spawn structures are cleaned after a number of days of use, e.g. every week if the spawn structures are removed daily.

In embodiments of all aspects of the invention, a first part of the spawn structure may remain free of eggs, while a second part of the spawn structure comprises the eggs. Advantageously, in such embodiments, the second part of the spawn structure comprising the eggs is removed from the spawning container and transported to the hatch area with a relatively high frequency, e.g. daily. The first part of the spawn structure may also periodically be replaced, but with a lower frequency, e.g. weekly.

In embodiments of all aspects of the invention, a preparation and cleaning facility is provided, adapted to remove the adult insects from the spawning containers, and to clean the spawning containers and to place new adult insects into the spawning containers. In method terms, the methods of all aspects of the invention may further comprise the steps: providing a preparation and cleaning facility, and periodically removing the adult insects from the spawning containers, cleaning the spawning containers and placing new adult insects into the spawning containers. Such cleaning is e.g. performed by a crate washer at elevated temperatures, e.g. up to ° C., and possibly involves a disinfecting step.

BRIEF DESCRIPTION OF THE FIGURES

All aspects of the invention will be elucidated further in relation to the attached drawings, in which:

FIG. 6a schematically represents the life cycle of a lesser mealworm in steps A-D;

FIG. 6b is a representation of a lesser mealworm beetle;

FIG. 6c is a schematic side view of a lesser mealworm beetle with a protracted egg-laying tube;

FIG. 7a is a highly schematic side view of part of a first embodiment of a spawn structure according to the third aspect of the present invention;

FIG. 7b is a highly schematic side view of part of an alternative embodiment of a spawn structure according to the third aspect of the present invention;

FIG. 8a is a side view of a second embodiment of a spawn structure according to the third aspect of the present invention;

FIG. 8b is a front view of the second embodiment of a spawn structure according to the third aspect of the present invention;

DETAILED DESCRIPTION OF THE INVENTION

Figure 1:
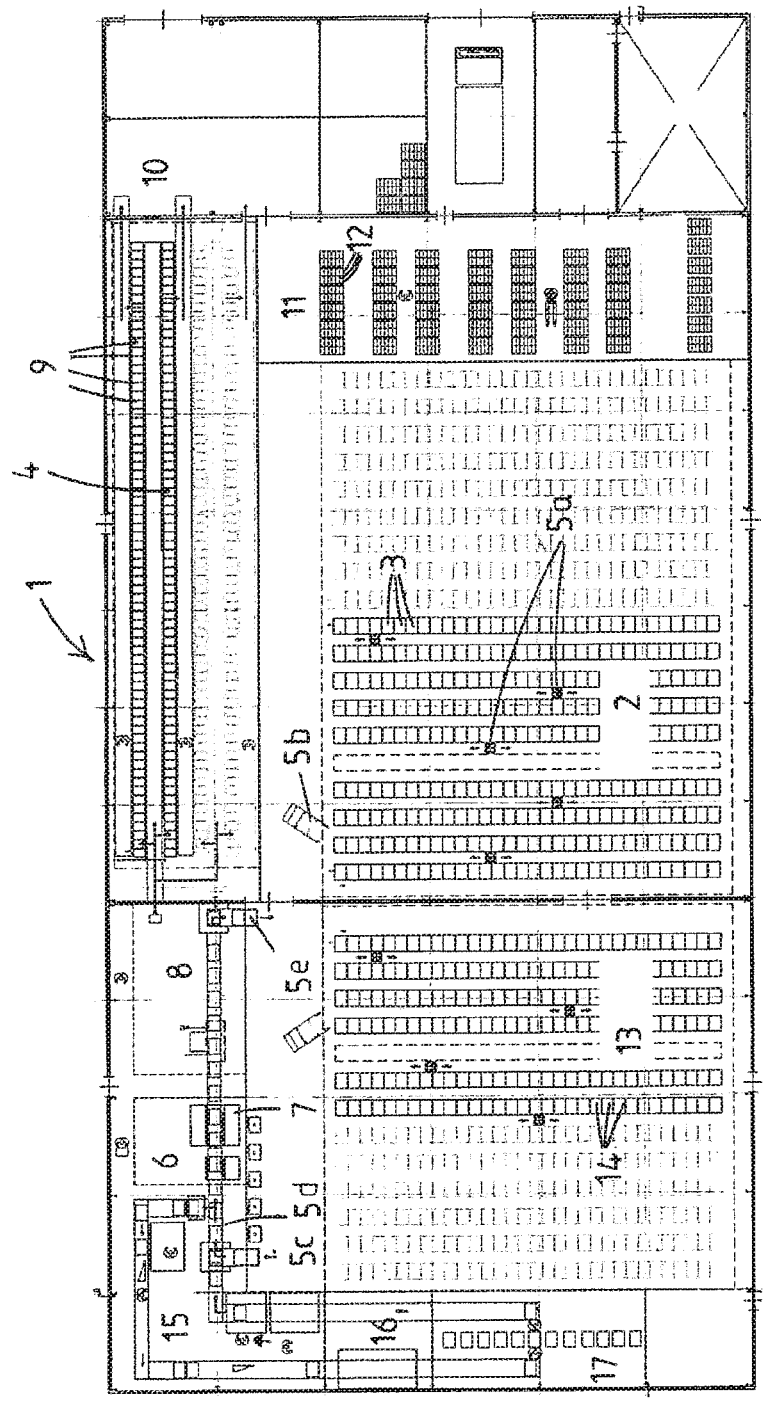
FIG. 1 represents a schematic insect breeding facility according to all aspects of the present invention.
Figure 2:
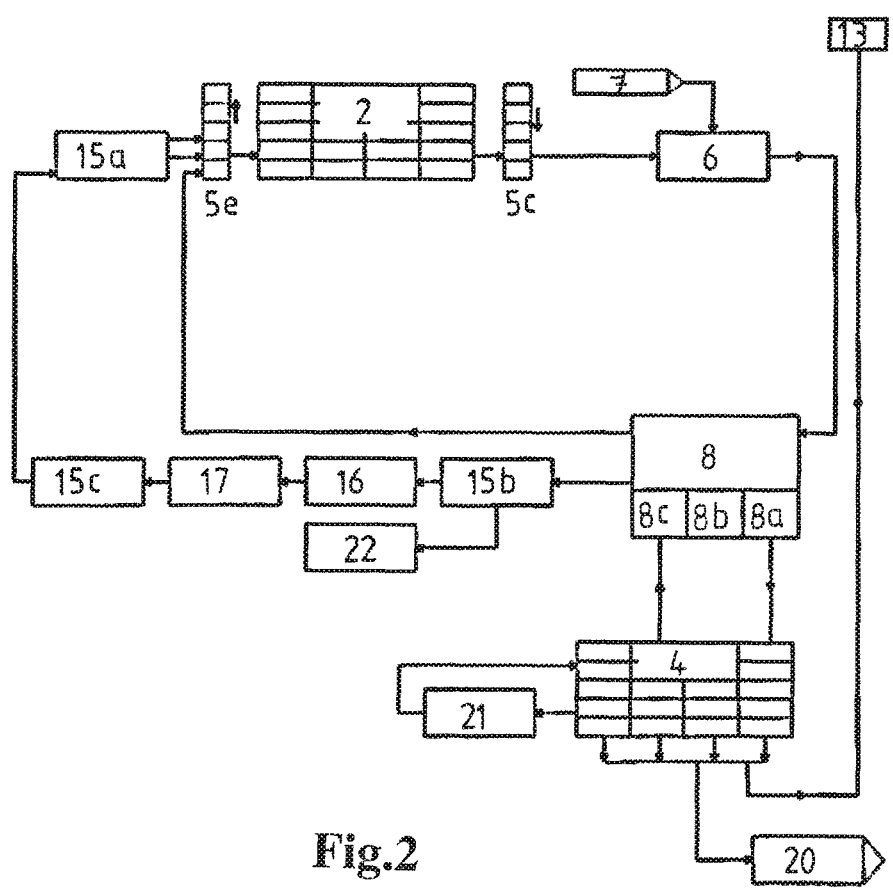
FIG. 2 represents a schematic flow chart of a method for breeding insects according to all aspects of the present invention.

In FIG. 1 an insect breeding facility 1 according to all aspects of the present invention is schematically represented. In FIG. 2 a flow chart of a method for breeding insects according to all aspects of the present invention is schematically shown.

Rows of stacked spawning containers 3, forming a plurality of batches of spawning containers, are provided in a spawning area 2, which spawning containers are adapted to receive adult insects and insect food. As will be explained in detail later in relation to FIGS. 3-5, in this spawning area each spawning container is provided with at least one spawn structure. In such spawn structures the mother insects will spawn their eggs such that the spawn structure or part of the spawn structure holds the eggs, wherein said spawn structure or said part thereof is removable from the spawning container, leaving the adult insects in the spawning container.

The insect breeding facility further comprises a hatch area 4 in which the eggs will hatch, which hatch area is adapted to receive the spawn structure or parts thereof holding the eggs, allowing periodical harvesting of baby larvae from the hatch area. In the shown embodiment, the hatch area 4 comprises a plurality of hatching chambers 9, each adapted to receive a number of spawn structures or parts thereof. According to the second aspect of the invention the number of hatching chambers corresponds to the number of batches of spawning containers 3. In the hatching chambers 9 the eggs will hatch, wherein an $n^{th}$ hatching chamber is adapted to receive the spawn structures or part of the spawn structures that hold the eggs of a corresponding $n^{th}$ batch of spawning containers.

The shown embodiment, according to the first aspect of the invention, comprises a container handling system 5a, 5b, 5c, 5d, 5e, adapted to periodically de-stack the one or more stacks and stack the spawning containers into one or more stacks, and to transport the spawning containers to a feeding area 6 comprising a food delivery system 7 to deliver food to the spawning containers. The shown container handling system comprises conveyors 5a for stacks of spawning containers, and automatically guided vehicles 5b to transport the stack of spawning containers to a de-stacking installation 5c. There, the individual spawning containers are placed onto a belt conveyor 5d, transporting the spawning containers to the feeding area 6 and an spawn structures handling area 8. At the end of the belt conveyor 5d, a stacking installation 5e is provided in which the spawning containers are stacked and prepared to be conveyed by an automatically guided vehicle 5b.

In the spawn structures handling area 8 a spawn structure handling system is provided, which is adapted to remove the spawn structure or parts thereof holding the eggs from the spawning container, in FIG. 2 schematically indicated with reference number 8a, and transport said spawn structure or said part to the hatch area 4. The spawn structure handling system is further adapted to provide an empty or clean spawn structure in each spawning container, in FIG. 2 schematically indicated with reference number 8c. Preferably, the spawn structure handling system is also adapted to clean a holder of the spawn structures, in FIG. 2 indicated with reference number 8b. In the schematic representation of FIG. 2, cleaning of the spawn structures is envisaged in a spawn structure cleaning facility 21 adjacent the hatch area 4. It is also conceivable that this spawn structure cleaning facility is provided instead of, or in addition to the spawn structure holder cleaning facility 8b.

In the hatch area 4, the eggs will hatch into baby larvae, which are periodically harvested as indicated with reference numeral 20 in FIG. 2. In the embodiment shown in FIG. 1, these baby larvae are transferred to a pre-rearing handling room 10 where the baby larvae are collected into baby larvae containers 12. These baby larvae containers are transferred to a pre-rearing area 11, in which the baby larvae remain several days to get stronger and grow to adolescent larvae. These adolescent larvae may be transferred to a remote rearing facility in which the adolescent larvae are tended to mature larvae, which are suitable for consumption.

Part of the adolescent larvae may also be transferred to a metamorphosis room 13, in which the adolescent larvae are tended to mature larvae followed by pupating and emerging into beetles. To this end, the adolescent larvae are transferred from the baby larvae containers 12 into pupating containers 14.

In the shown embodiment, the container handling system 5a-5e is also adapted to handle the pupating containers with conveyors 5a for the containers, and automatically guided vehicles 5b to transport the containers to a de-stacking installation 5c. There, the individual pupating containers 14 are placed onto a belt conveyor 5d, transporting the pupating containers 14 to a separation and preparation facility 15, in which the beetles are separated from the pupating containers and placed into new and empty spawning containers, indicated with reference number 15a in FIG. 2. In FIG. 2, the different functions of the separation and preparation facility 15 are elucidated. The beetles are separated from excrements and other possible remainders e.g. by sifting and shifting machines.

The remaining content of the container, i.e. food and residue such as droppings is removed from the pupating container and the pupating containers are transported to a cleaning facility 16 for cleaning the containers. A container buffer 17 is advantageously provided for the storage of redundant containers.

Spawning containers that have spent sufficient time in the spawning area 2, and of which the egg production has reduced below a threshold, are also transported by the belt conveyor 5d to the separation and preparation facility 15, where the content of the container, i.e. beetles and food is removed from the spawning container, indicated with reference numbers 15b and 22 in FIG. 2, and the spawning container is transported to a cleaning facility 16 for cleaning the containers. A container buffer 17 is provided for the storage of redundant containers. Spawning containers may be prepared in step 15c to receive beetles in step 15a.

Figures 3A, 3B:
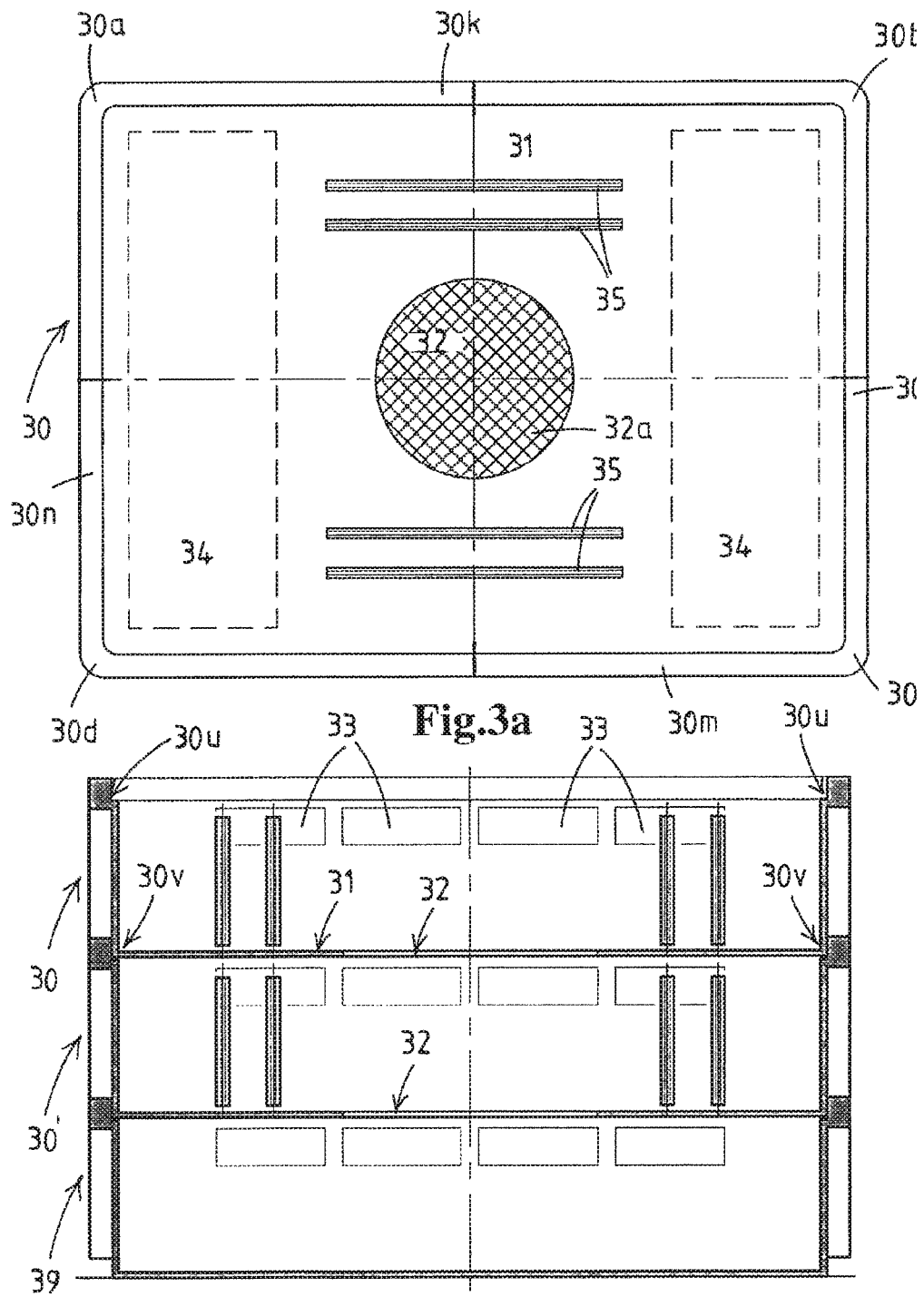
FIG. 3a is a top view of a first embodiment of a spawning container.
FIG. 3b is a cross-sectional side view of a stack of spawning containers of the first embodiment.
Figure 3C:
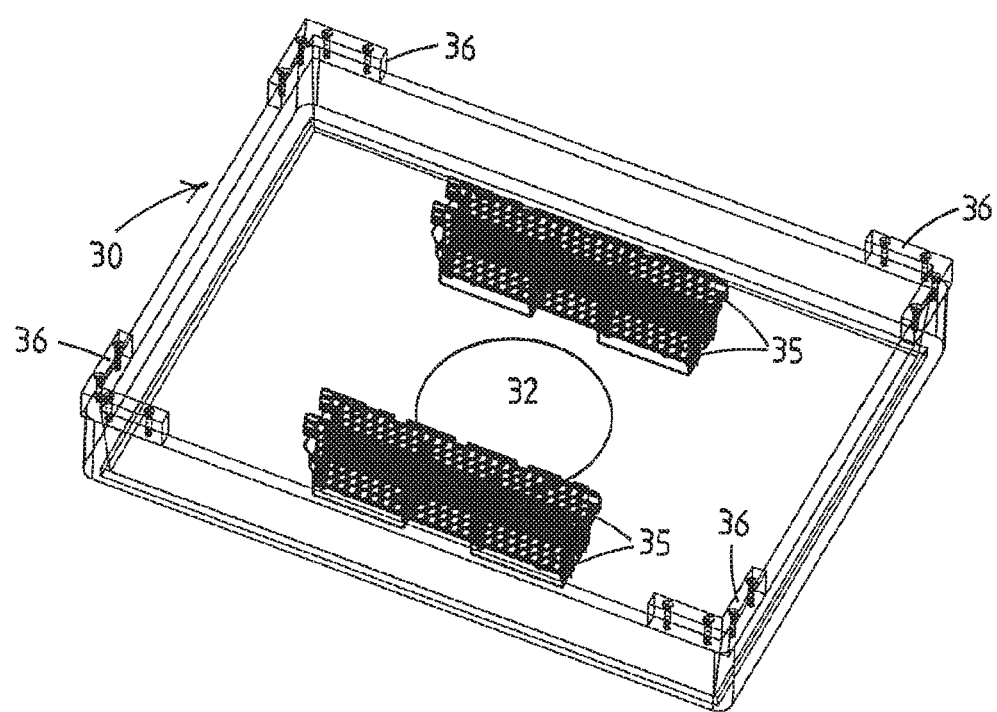
FIG. 3c is a perspective view of an embodiment similar to the first embodiment of the spawning container.

In FIGS. 3a-3b, a first embodiment of a spawning container 30 according to all aspects of the present invention is indicated in various views. In FIG. 3c, an embodiment similar to the first embodiment is shown. The spawning container 30 is of an essentially rectangular shape comprising four corners 30a, 30b, 30c, 30d, between which a peripheral wall, here comprising four sides 30k, 30l, 30m, 30n, is provided, wherein the corner portions have a configuration that allows stacking of the trays and provide sufficient strength for heavy loads of stacked trays. In the cross-sectional side view of FIG. 3b, it is visible that the corner portions define an upper corner support surface 30u, onto which a bottom corner support surface 30v can be stacked due to the interlocking configurations. In the embodiment of FIG. 3c, stacking elements 36 are provided at the corner portions to allow stacking of the trays.

The spawning container 30 comprises a bottom 31, provided with a perforated area 32 to allow the removal of excrements. In FIG. 3b, a stack of spawning containers 30, 30' is shown, below which an excrement collection tray 39 is positioned. The perforated area has preferably openings 32a of a dimension allowing the removal of excrements, but preventing adult insects from getting trapped.

In the embodiments of FIGS. 3a and 3b, the spawning container 30 comprises a peripheral wall 30k-30n provided with ventilation openings 33 to allow for the dissipation of heat and $CO_2$.

In the shown embodiment, the spawning container 30 is also provided with dedicated feeding zones 34 remote from the perforated bottom areas 32.

According to all aspects of the present invention, the spawning container 30 is provided with a spawn structure 35, here four spawn structures 35, in which spawn structures the mother insects will spawn their eggs such that the spawn structure or part of the spawn structure holds the eggs, wherein said spawn structure or said part thereof is removable from the spawning container, leaving the adult insects in the spawning container. The spawn structures are positioned remote from the feeding zones 34 and from the perforated bottom areas 32.

Figure 4A:
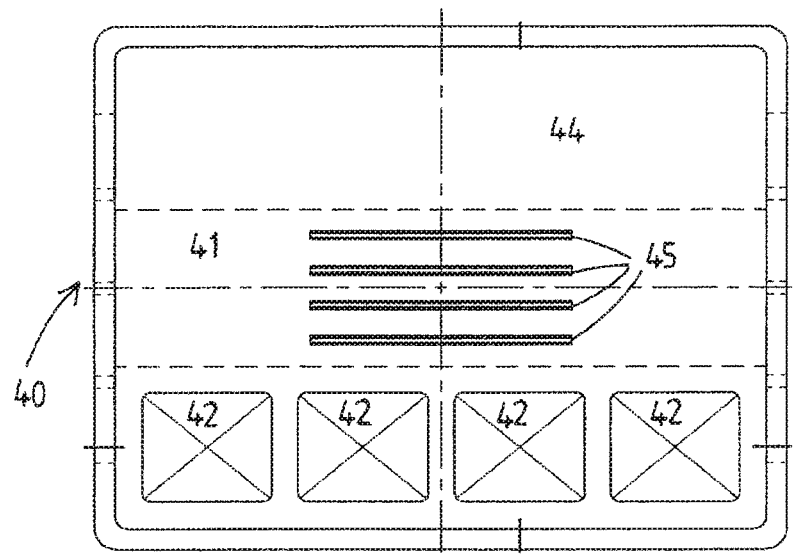
FIG. 4a is a top view of a second embodiment of a spawning container.
Figure 4B:
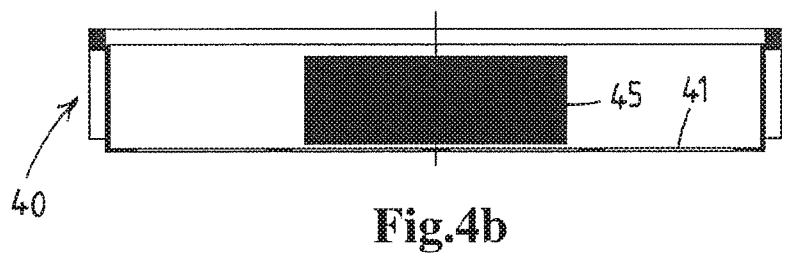
FIG. 4b is a cross-sectional side view of the second embodiment.
Figure 4C:
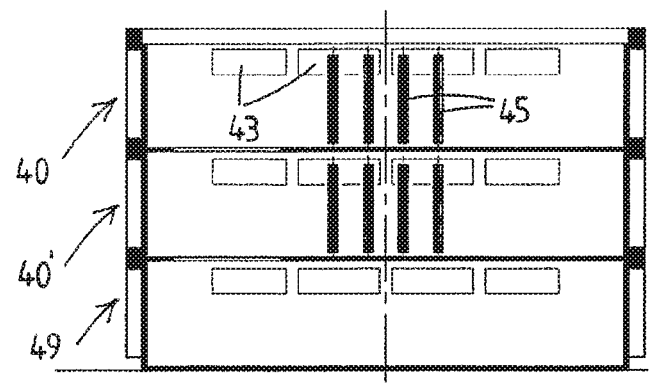
FIG. 4c is a cross-sectional side view of a stack of spawning containers of the second embodiment.

In FIGS. 4a-4c, a second embodiment of a spawning container 40 according to all aspects of the present invention is indicated in various views. The shape of spawning container 40 essentially corresponds to that of spawning container 30, having four corners between which a peripheral wall is provided, wherein the corner portions have a configuration that allows stacking of the trays and provide sufficient strength for heavy loads of stacked trays. Spawning container 40 comprises ventilation openings 43 to allow for the dissipation of heat and $CO_2$.

The spawning container 40 comprises a bottom 41, provided with four perforated areas 42 to allow the removal of excrements. In FIG. 4c, a stack of spawning containers 40, 40' is shown, below which an excrement collection tray 49 is positioned.

In the shown embodiment, the spawning container 40 is also provided with a dedicated feeding zone 44 remote from the perforated bottom areas 42.

According to all aspects of the present invention, the spawning container 40 is provided with a spawn structure 45, here four spawn structures 45, in which spawn structures the mother insects will spawn their eggs such that the spawn structure or part of the spawn structure holds the eggs, wherein said spawn structure or said part thereof is removable from the spawning container, leaving the adult insects in the spawning container. The spawn structures are positioned remote from the perforated bottom areas 42 and the feeding zone 44.

Figure 5A:
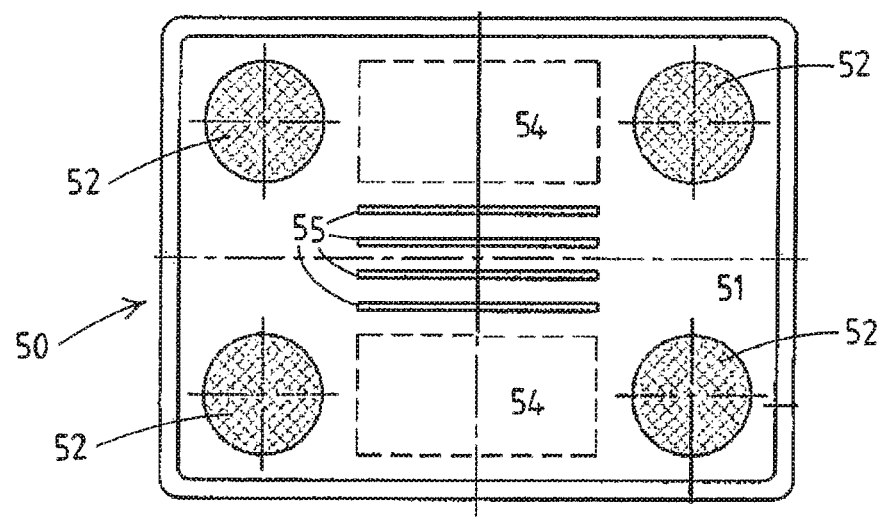
FIG. 5a is a top view of a third embodiment of a spawning container.
Figure 5B:
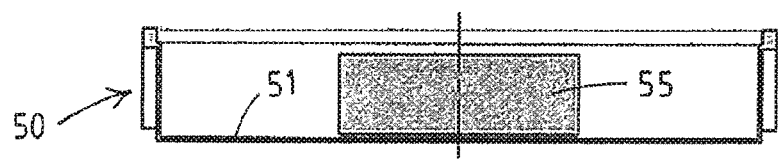
FIG. 5b is a cross-sectional side view of the third embodiment.
Figure 5C:
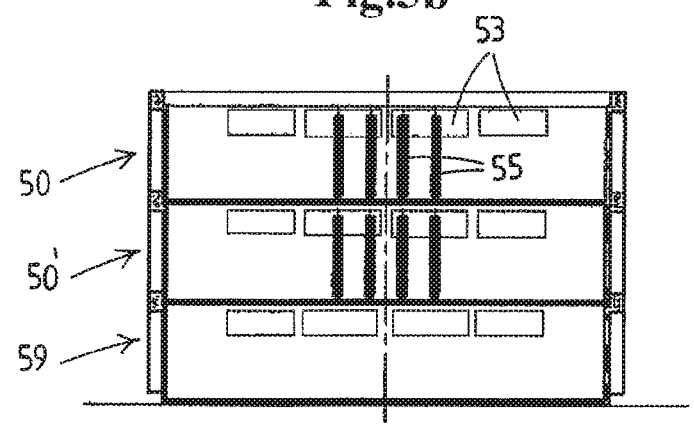
FIG. 5c is a cross-sectional side view of a stack of spawning containers of the third embodiment.

In FIGS. 5a-5c, a third embodiment of a spawning container 50 according to all aspects of the present invention is indicated in various views. The shape of spawning container 50 essentially corresponds to that of spawning container 30, having four corners between which a peripheral wall is provided, wherein the corner portions have a configuration that allows stacking of the trays and provide sufficient strength for heavy loads of stacked trays. Spawning container 50 comprises ventilation openings 53 to allow for the dissipation of heat and $CO_2$.

The spawning container 50 comprises a bottom 51, provided with four perforated areas 52 to allow the removal of excrements. In FIG. 5c, a stack of spawning containers 50, 50' is shown, below which an excrement collection tray 59 is positioned.

In the shown embodiment, the spawning container 50 is also provided with dedicated feeding zones 54 remote from the perforated bottom areas 52.

According to all aspects of the present invention, the spawning container 50 is provided with a spawn structure 55, here four spawn structures 55, in which spawn structures the mother insects will spawn their eggs such that the spawn structure or part of the spawn structure holds the eggs, wherein said spawn structure or said part thereof is removable from the spawning container, leaving the adult insects in the spawning container. The spawn structures are positioned remote from the perforated bottom areas 52 and the feeding zones 54.

In FIGS. 6a-6c a lesser mealworm is shown, which is an insect in particular adapted to be bred in the insect breeding facility and with the insect breeding method according to all aspects of the invention. In FIG. 6a, the life cycle of a lesser mealworm is shown in steps, wherein the adult beetle is referred to with reference letter A. This adult beetle is shown in an enlarged view in FIG. 6b, and in a schematic side view in FIG. 6c. In this view, a protracted egg-laying tube 100 is clearly visible. The adult beetle deposits eggs, indicated with reference letter B. These eggs hatch into baby larvae, indicated with the letter C, which molts before it enters the pupal stage, indicated with reference letter D.

In FIGS. 7a and 7b highly schematic side views of part of alternative spawn structures 60, 70 according to the third aspect of the present invention are shown. In the spawn structures 60, 70, the mother insects will spawn their eggs B. The spawn structure 60, 70 comprises a first part 61, 71 and a second part 62, 72 which are movable with respect to each other allowing an increase and decrease of the mutual distance. In FIGS. 7a and 7b, the first and a second part of the spawn structures 60, 70 are positioned with respect to each other such that a multitude of crevices 63, 73 is created therebetween. In the partial views of FIGS. 7a and 7b, two crevices are visible adjacent openings 64, 74 in the first parts of the spawn structures, which are possibly elongated. In addition, crevices also arise at the top and bottom of the spawn structures 60, 70. Mother insects may also spawn their eggs B into these crevices. According to all aspects of the present invention, the part or parts of the spawn structure that holds the eggs B is removable from the spawning container, leaving the adult insects in the spawning container. In the shown embodiment, for the purpose of hatching the distance between the first 61, 71 and second part 62, 72 of the spawn structure is 60, 70 adapted to be increased to enlarge the area around the eggs.

Figure 8C:
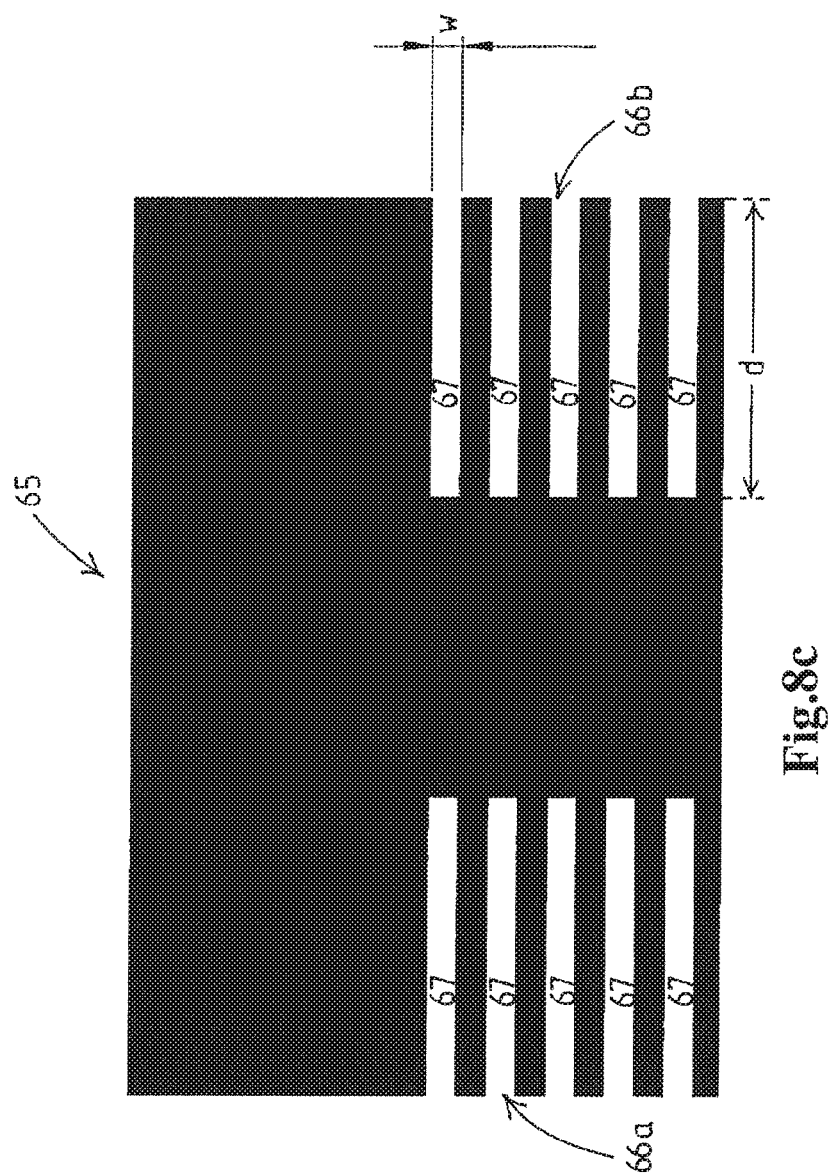
FIG. 8c is a detail of the side view of the second embodiment of a spawn structure according to the third aspect of the present invention.

In FIGS. 8a-8c a second embodiment of a spawn structure 65 according to the third aspect of the present invention is schematically shown. The spawn structure 65 has opposed faces 66a, 66b, wherein face 66a is visible in a front view in FIG. 8b, which faces 66a, 66b are positioned as scalable faces in an insect spawning container (not shown), such that crawling mother beetles having a protractable egg-laying tube, such as lesser mealworms or *Zophobas* morios can crawl from the bottom of the container onto and up along the scalable face of the spawn structure. The spawn structure 65 is possible positioned vertically upright in the spawning container, resulting in two vertical scalable faces 66a, 66b. The spawn structure 65 can also be positioned at an angle with the vertical, which may result in two or just one scalable face 66a, 66b.

Spawn structure 65 comprises a multitude of crevices 67, accessible from the scalable faces 66a, 66b, in particular allowing the entry of the egg-laying tube of the mother beetles. The crevices 67 have dimensions, in particular a width w and a depth d, which are tuned to the egg-laying tube of the mother beetles. For breeding lesser mealworms, the width w of the crevices is 0.2-1.2 mm, preferably 0.5 mm. For breeding *Zophobas* morios, the width of the crevices is 0.2-1.8 mm, preferably about 1.0 mm. The depth of the crevices of the shown embodiment is about 8 times the width, and may thus be 4-10 mm. The length of the crevices in the shown embodiment extend over the entire spawn structure, allowing multiple mother beetles to deposit their eggs adjacent each other.

It is noticed that the crevices according to the third aspect of the present invention are accessible from the scalable face. In embodiments, as shown in FIGS. 8a-8c, the crevices extend essentially perpendicular to the scalable face. It is also conceivable that the crevices extend at an angle, e.g. 30-70°, either in an upward direction with respect to the scalable face or in a downward direction.

Figure 9A:
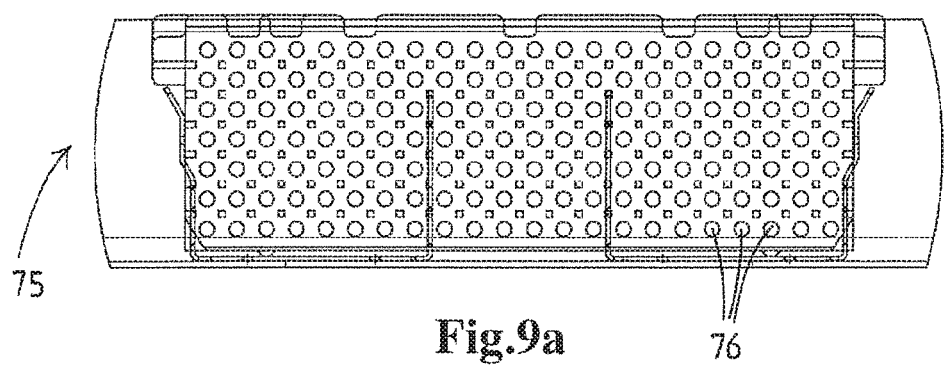
FIG. 9a shows a side view of a third embodiment of a spawn structure according to the third aspect of the invention.
Figure 9B:
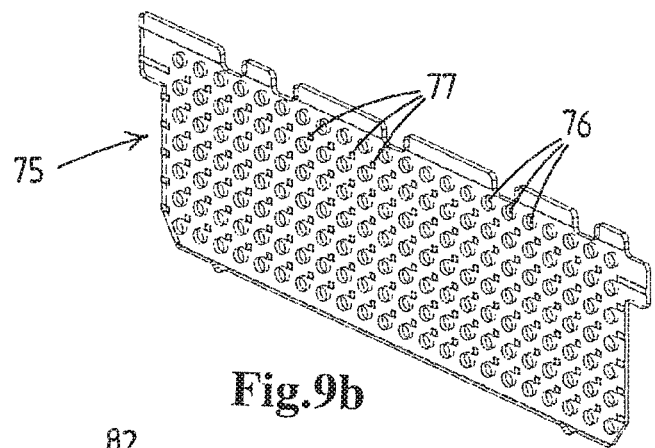
FIG. 9b shows a perspective view of the third embodiment of a spawn structure according to the third aspect of the invention.

In FIGS. 9a-9b a plate-shaped first part 75 which is part of a third embodiment of a spawn structure according to the third aspect of the invention is shown in different positions. This is explained in more detail in relation to FIG. 10.

Figure 10:
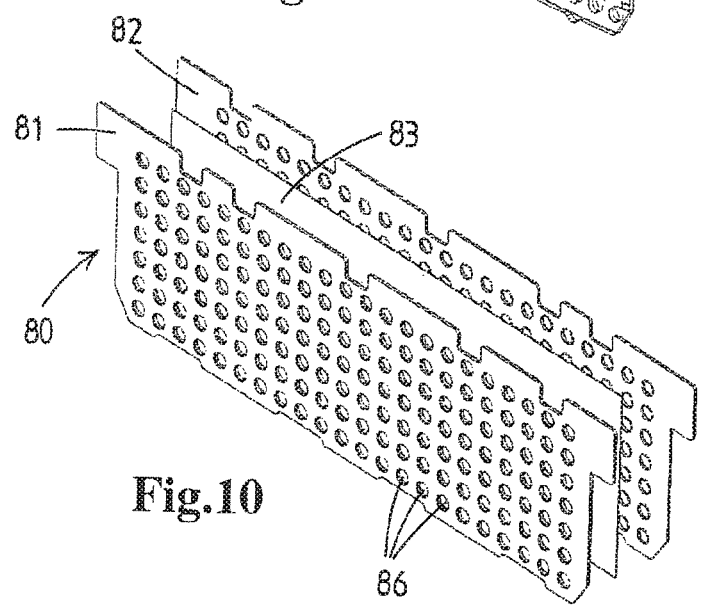
FIG. 10 shows a perspective view of a fourth embodiment of a spawn structure according to the third aspect of the invention wherein the first and second part of the spawn structure are positioned at a distance from each other.

In FIG. 10 a fourth embodiment of a spawn structure 80 according to the third aspect of the invention is shown, for breeding insects of the type with crawling mother beetles having a protractable egg-laying tube, such as lesser mealworms or *Zophobas* morios. The beetles have an egg-laying tube which can be protracted, as visible in FIG. 6c. Such insects prefer to spawn their eggs into crevices, in which the eggs are stuck to a surface. The embodiment of the spawn structure 80 of FIG. 9 provides an assembly of three plate-shaped parts, in particular first parts 81, 82 and a second part 83 which are movable with respect to each other allowing an increase and decrease of the mutual distance. It is noted that it is equally conceivable that only one first part 81 is provided.

Figure 11:
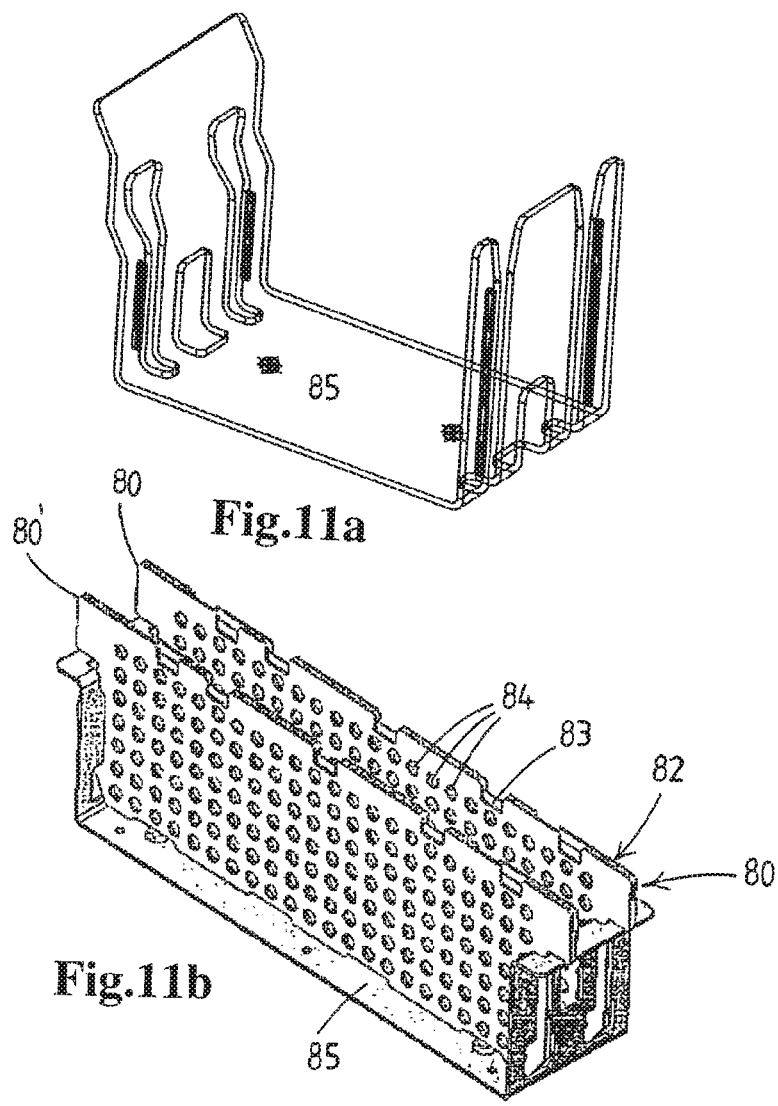
FIG. 11a shows a perspective view a spawn structure holder.
FIG. 11b shows a perspective view of a spawn structure holder comprising two spawn structures.

In a spawn structure holder 85 such as visible in FIGS. 11a and 11b, the first parts 81, 82 and second part 83 of the spawn structure 80 are positioned with respect to each other such that a multitude of crevices 84 is created therebetween, which is the position suitable for the purpose of spawning. In particular, the first parts 81, 82 are provided with cut-aways 86 to create the multitude of crevices 84 between the plates. The plates 81, 82 and 83 are positioned at a small mutual distance, e.g. 0.2-1.2 mm, creating crevices between the outer contour of cut-away 86 and second plate 83. In the shown embodiment of FIGS. 10 and 11, the cut-aways 86 have a circular shape. It is also conceivable that the cut-away is embodied as a slit or more zig-zag-shaped, or shaped as a wave. As the crevices 84 are created between the first and second plate, the crevices are also created at the top, bottom and side ends of the spawn structure 80. To allow successful spawning of the mother beetles, the crevice that is created has a dimension allowing the entry and passage of a protracted egg-laying tube of the beetle into the crevice, to deposit her eggs in the crevices onto the first and/or second part of the spawn structures during spawning. Advantageously, the dimension of the crevice prohibits the entry of the mouth into the crevice, and thus prevents the beetles to eat the eggs.

According to the third aspect of the invention, the distance between the first part 81, 82 and second part 83 of the spawn structure 80 can be increased to enlarge the area around the eggs prior to hatching the eggs. This is shown in FIG. 10. It is equally conceivable that this increase of the mutual distance takes place prior to or after the removal of the spawn structure 80 from the spawning container.

In embodiments, the side of the crevices adjacent first parts 81, 82 is made non-sticking, as a result of which all eggs stick to the second part 83 of the spawn structure 80. As a result, only this second part 83 is to be removed from the spawning container and transported to the hatch area. Alternatively, the side of the crevices adjacent second part 83 is made non-sticking, as a result of which all eggs stick to the first parts 81, 82 of the spawn structure 80. As a result, these first parts 81, 82 are to be removed from the spawning container and transported to the hatch area. In the embodiment of the plate-shaped first part 75 as shown in FIGS. 9a-9b, crevices are also created between the outer contour of circular cut-away 76 and a not shown second plate. Between the cut-aways 76 square-shaped protrusions 77 are visible, which protrude in the direction of the not-shown second plate, in order to position a non-sticking medium onto the second plate. Accordingly, the eggs will stick on the shown first part 75 of the spawn structure.

According to the third aspect of the invention an empty or clean spawn structure is provided in each spawning container by the spawn structure handling system. It is conceivable that only a new or clean second part of the spawn structure is placed between the first plates 81, 82, or that the entire spawn structure is replaced and that the first plates are cleaned.

In FIGS. 11a and 11b, spawn structure holders 85 are shown, which can be mounted to or formed integral with the spawning container (not shown). The spawn structure holder 85 as shown is adapted to hold two spawn structures 80, 80'. The spawn structures 80, 80' are held at a selected mutual distance. In the shown embodiment, the entire spawn structures 80, 80' are removable from the spawn structure holder 85, leaving the adult insects in the spawning container.

Figure 12:
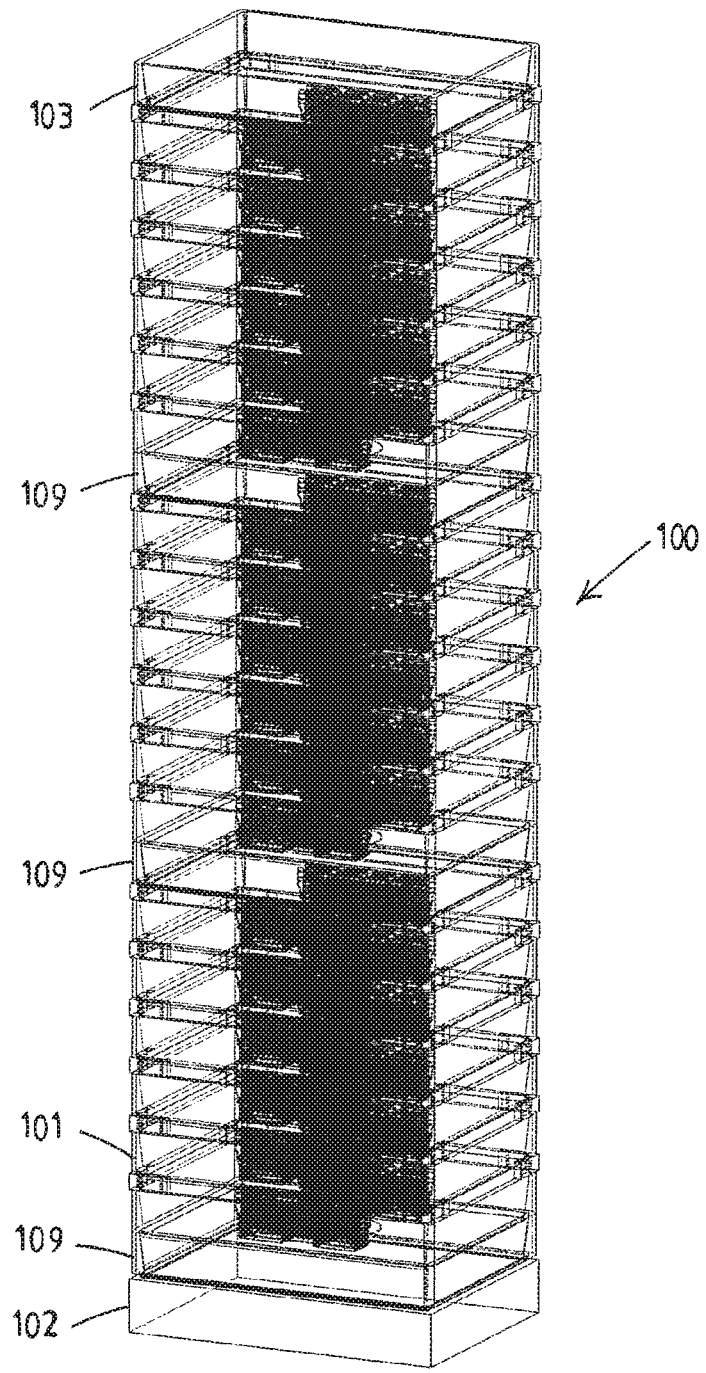
FIG. 12 shows a stack of spawning containers.

In FIG. 12, a stack 100 of 18 spawning containers 101, positioned on a pallet 102 is shown in a perspective view. Below every 6 spawning containers, an excrement collection container 109 is positioned. On top of the stack, a lid 103 is positioned. Each container is provided with four spawn structures, similar to the embodiment of FIG. 3c.

Figure 13A:
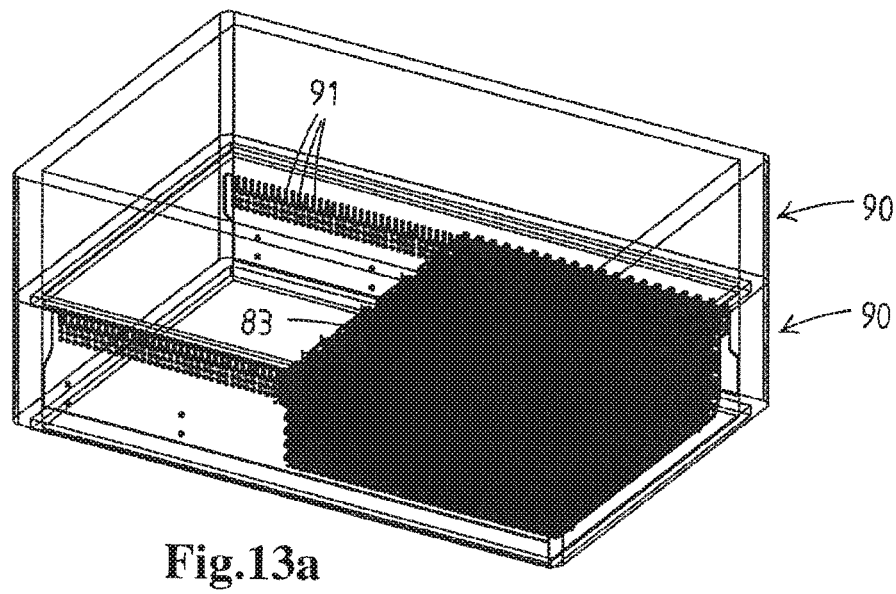
FIG. 13a shows a perspective view of a hatching container partly filled with parts of spawn structures that hold the eggs.
Figure 13B:
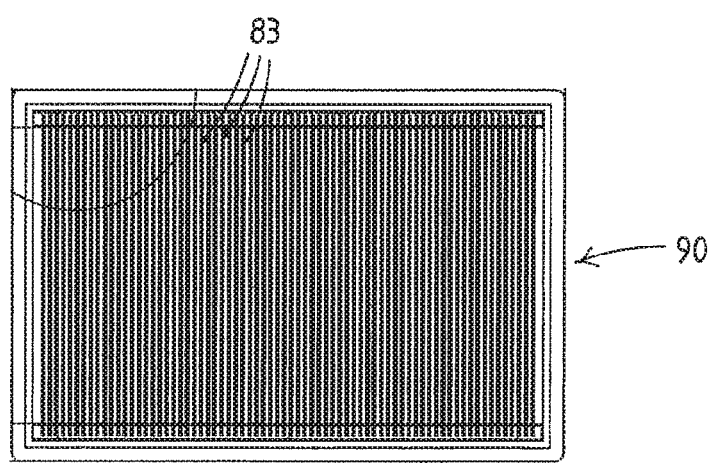
FIG. 13b shows a top view of the hatching container of FIG. 13a with a plurality of parts of a spawn structure that hold the eggs.

In this third embodiment of a spawn structure, a part of the spawn structure hold the eggs, and is thus to be removed from the spawning container and transported to the hatch area. In FIGS. 13a and 13b, a possible embodiment of a hatching container 90 is shown, adapted to receive multiple parts 83 of spawn structures 80 that hold the eggs. In FIG. 13a, plate receiving slits 91 are visible, adapted to receive the plate-shaped parts 83 of the spawn structure 80 that hold the eggs. In FIGS. 13a and 13b, the hatching container 90 is shown comprising a plurality of parts 83 of the spawn structure 80 that hold the eggs. The configuration of the hatching container is such that multiple hatching containers 90 may be stacked on top of each other in the hatch area or in a hatching chamber. A baby larvae collection container may be provided below each hatching container or each stack of hatching containers.

The invention claimed is:

1. Insect spawning container to be used in an insect breeding facility for breeding insects of the type with crawling mother beetles having a protractable egg-laying tube, in which insect spawning container at least one spawn structure is provided in which the mother insects will spawn their eggs, wherein the insect spawning container comprises a bottom, and the at least one spawn structure adjoins the bottom, the at least one spawn structure having a scalable face such that the mother beetles can crawl from the bottom onto and up along the scalable face of the spawn structure, and the at least one spawn structure comprising a multitude of crevices accessible from the scalable face, the crevices having dimensions tuned to the egg-laying tube of the mother beetles.

2. Insect spawning container according to claim 1, wherein for breeding lesser mealworms the width of the crevices is 0.2-1.2 mm, and for breeding *Zophobas morios* the width of the crevices is 0.2-1.8 mm.

3. Insect spawning container according to claim 1, wherein the depth of the crevices is 0.5-10.0 mm.

4. Insect spawning container according to claim 1, wherein the bottom of the spawning container is provided with a perforated area to allow the removal of excrements.

5. Insect spawning container according to claim 1, wherein crevices are embodied as elongated slits.

6. Insect spawning container according to claim 1.

7. Insect spawning container to be used in an insect breeding facility for breeding insects of the type with crawling mother beetles having a protractable egg-laying tube, the spawning container being provided with at least one spawn structure, in which spawn structure the mother insects will spawn their eggs, the spawn structure comprising a first part and a second part which are movable with respect to each other allowing an increase and decrease of the mutual distance, wherein for the purpose of spawning the first and a second part of the spawn structures are positionable with respect to each other such that a multitude of crevices is created therebetween, and wherein for the purpose of hatching and/or cleaning the distance between the first and second part of the spawn structure is adapted to be increased.

8. Insect spawning container according to claim 7, wherein the first and second part of the spawn structure are embodied as plates.

9. Insect spawning container according to claim 8, wherein the plates are placed at a small distance from each other, and wherein in the first plate cut-aways are provided to create a multitude of crevices between the plates.

10. Insect spawning container according to claim 7, wherein crevices are embodied as elongated slits.

11. Insect breeding facility for breeding insects of the type with crawling mother beetles having a protractable egg-laying tube, comprising:
   a spawning area in which a plurality of spawning containers are present which are adapted to receive or have received adult insects including mother insects and insect food;
   a plurality of spawn structures, wherein at least one spawn structure is adapted to be provided or is provided in each spawning container in the spawning area, in which spawn structures the mother insects will spawn their eggs such that the spawn structure or part of the spawn structure holds the eggs, wherein said spawn structure or said part thereof is removable from the spawning container, leaving the adult insects in the spawning container;
   a hatch area in which the eggs will hatch, which hatch area is adapted to receive said spawn structure or said part thereof holding the eggs and removed from the spawning containers, allowing harvesting of baby larvae;
   a food delivery system to deliver food to the spawning containers;
   a spawn structures handling area comprising a spawn structure handling system, adapted to remove said spawn structure or said part thereof holding the eggs from the spawning container, leaving the adult insects in the spawning container, and transport said spawn structure or said part to the hatch area, and to provide an empty spawn structure or part thereof in each spawning container;
   a container handling system to transport the spawning containers between the spawning area and the spawn structures handling area.

12. Insect breeding facility according to claim 11, comprising one or more spawning containers, each spawning container to be used in an insect breeding facility for breeding insects of the type with crawling mother beetles having a protractable egg-laying tube, in which insect spawning container at least one spawn structure is provided in which the mother insects will spawn their eggs, wherein the insect spawning container comprises a bottom, and the at least one spawn structure adjoins the bottom, the at least one spawn structure having a scalable face such that the mother beetles can crawl from the bottom onto and up along the scalable face of the spawn structure, and the at least one spawn structure comprising a multitude of crevices accessible from the scalable face, the crevices having dimensions tuned to the egg-laying tube of the mother beetles.

13. Insect breeding facility for breeding insects of the type with crawling mother beetles having a protractable egg-laying tube, comprising:
   a spawning area in which a plurality of spawning containers are present which 5 are adapted to receive or have received adult insects including mother insects and insect food;
   a plurality of spawn structures, wherein at least one spawn structure is adapted to be provided or is provided in each spawning container in the spawning area, in which spawn structures the mother insects will spawn their eggs such that the spawn structure or part of the spawn structure holds the eggs, wherein said spawn structure or said part thereof is removable from the spawning container, leaving the adult insects in the spawning container, wherein each spawn structure comprises a first part and a second part which are movable with respect to each other allowing an increase and decrease of the mutual distance,
   wherein for the purpose of spawning the first and a second part of the spawn structure are positionable with respect to each other such that a multitude of crevices is created therebetween;
   and wherein for the purpose of hatching and/or cleaning the distance between the first and second part of the spawn structure is adapted to be 20 increased;
   a hatch area in which the eggs will hatch, which hatch area is adapted to receive said spawn structure or said part thereof holding the eggs and removed from the spawning containers, allowing harvesting of baby larvae;
   a food delivery system to deliver food to the spawning containers;
   a spawn structures handling area comprising a spawn structure handling system, adapted to remove said spawn structure or said part thereof holding the eggs from the spawning container, leaving the adult insects in the spawning container, and transport said spawn structure or said part to the hatch area, and to provide an empty spawn structure or part thereof in each spawning container;
   a container handling system to transport the spawning containers between the spawning area and the spawn structures handling area.

14. Method for breeding insects of the type with crawling mother beetles having a protractable egg-laying tube, comprising the steps of:
   providing a spawning area in which a plurality of spawning containers, are present which have received adult insects including mother insects and which are adapted to receive or have received insect food;
   providing at least one spawn structure in each spawning container in the spawning area, in which spawn structure the mother insects will spawn their eggs such that the spawn structure or part of the spawn structure holds the eggs, wherein said spawn structure or part thereof is removable from the spawning container, leaving the adult insects in the spawning container;
   providing a hatch area in which the eggs will hatch, which hatch area is adapted to receive said spawn structure or said part thereof holding the eggs and removed from the spawning containers, allowing harvesting of baby larvae;
   providing a food delivery system to deliver food to the spawning containers; providing a spawn structures handling area comprising a spawn structure handling system, adapted to remove said spawn structure or said part thereof holding the eggs from the spawning container, leaving the adult insects in the spawning container, and transport said spawn structure or said part to the hatch area, and to provide an empty spawn structure or part thereof in each spawning container;
   providing a container handling system to transport the spawning containers between the spawning area and the spawn structures handling area;
   the mother beetles spawning their eggs,
   periodically:
      delivering food to the spawning containers;
      transporting the spawning containers from the spawning area to the spawn structures handling area;

removing the spawn structures or parts thereof holding the eggs from the spawning containers by the spawn structure handling system, leaving the adult insects in the spawning container;

transporting said spawn structures or said parts thereof to the hatch area by the spawn structure handling system;

providing an empty spawn structures or parts thereof in each spawning container by the spawn structures handling system;

transporting the spawning containers from the spawn structures handling area to the spawning area by the container handling system;

hatching the eggs in the hatch area, and periodically harvesting baby larvae.

15. Method according to claim 14, wherein the insect spawning container comprises a bottom, and the at least one spawn structure adjoins the bottom, and wherein the spawn structure in the spawning container in the spawning area has a scalable face such that the mother beetles can crawl from the bottom onto and up along the scalable face of the spawn structure, and the at least one spawn structure comprising a multitude of crevices accessible from the scalable face, the crevices having dimensions tuned to the egg-laying tube of the mother beetles.

16. Method according to claim 14, wherein use is made of one or more spawning containers, each spawning container to be used in an insect breeding facility for breeding insects of the type with crawling mother beetles having a protractable egg-laying tube, in which insect spawning container at least one spawn structure is provided in which the mother insects will spawn their eggs, wherein the insect spawning container comprises a bottom, and the at least one spawn structure adjoins the bottom, the at least one spawn structure having a scalable face such that the mother beetles can crawl from the bottom onto and up along the scalable face of the spawn structure, and the at least one spawn structure comprising a multitude of crevices accessible from the scalable face, the crevices having dimensions tuned to the egg-laying tube of the mother beetles.

17. Method for breeding insects of the type with crawling mother beetles having a protractable egg-laying tube, comprising the steps of:

providing a spawning area in which a plurality of spawning containers are present which have received adult insects including mother insects and which are adapted to receive or have received insect food;

providing at least one spawn structure in each spawning container in the spawning area, in which spawn structure the mother insects will spawn their eggs such that the spawn structure or part of the spawn structure holds the eggs, wherein said spawn structure or part thereof is removable from the spawning container, leaving the adult insects in the spawning container; wherein each spawn structure comprises a first part and a second part which are movable with respect to each other allowing an increase and decrease of the mutual distance, providing a hatch area in which the eggs will hatch, which hatch area is adapted to receive said spawn structure or said part thereof holding the eggs and removed from the spawning containers, allowing harvesting of baby larvae;

providing a food delivery system to deliver food to the spawning containers;

providing a spawn structures handling area comprising a spawn structure handling system, adapted to remove said spawn structure or said part thereof holding the eggs from the spawning container, leaving the adult insects in the spawning container, and transport said spawn structure or said part to the hatch area, and to provide an empty spawn structure or part thereof in each spawning container;

providing a container handling system to transport the spawning containers between the spawning area and the spawn structures handling area; positioning the first and a second part of the spawn structures with respect to each other such that a multitude of crevices is created therebetween, allowing the mother beetles to spawn their eggs in the crevices onto the first and/or second part of the spawn structures, periodically:
 delivering food to the spawning containers;
 transporting the spawning containers from the spawning area to the spawn structures handling area;
 increasing the distance between the first and second part of the spawn structure,
 removing the spawn structures or parts thereof holding the eggs from the spawning containers by the spawn structure handling system, leaving the adult insects in the spawning container;
 transporting said spawn structures or said parts thereof to the hatch area by the spawn structure handling system;
 providing an empty spawn structures or parts thereof in each spawning container by the spawn structures handling system;
 transporting the spawning containers from the spawn structures handling area to the spawning area by the container handling system;

hatching the eggs in the hatch area, and periodically harvesting baby larvae.

18. Method according to claim 17, wherein in the spawn structures handling area the entire spawn structure is removed from the spawning container, and wherein in a subsequent step the distance between the parts of the spawn structure is increased, allowing the first and/or second part of the spawn structure comprising the eggs to be transported to the hatch area.

19. Method according to claim 17, wherein the first part of the spawn structure is non-sticking, and the eggs are spawned onto the second part of the spawn structure, and wherein the first and second part of the spawn structure are provided movable with respect to each other in the spawning container, allowing the distance between the first and second part of the spawn structure to be increased in the spawning container in the spawn structures handling area prior to removing the second part of the spawn structure comprising the eggs from the spawning container and transporting said second part of the spawn structure comprising the eggs from the spawning container to the hatch area.

* * * * *